US012716066B2

(12) United States Patent
Nam et al.

(10) Patent No.: US 12,716,066 B2
(45) **Date of Patent: *Aug. 25, 2026**

(54) PHARMACEUTICAL COMPOSITION CONTAINING HERES EXPRESSION INHIBITOR FOR PREVENTING OR TREATING SQUAMOUS CELL CARCINOMA

(71) Applicants: IUCF-HYU (INDUSTRY-UNIVERSITY COOPERATION FOUNDATION HANYANG UNIVERSITY), Seoul (KR); INDUSTRY-ACADEMIC COOPERATION FOUNDATION, YONSEI UNIVERSITY, Seoul (KR)

(72) Inventors: Jin-Wu Nam, Seoul (KR); Bo-Hyun You, Seoul (KR); Sang Kil Lee, Seoul (KR); Jung Ho Yoon, Seoul (KR)

(73) Assignees: IUCF-HYU (INDUSTRY-UNIVERSITY COOPERATION FOUNDATION HANYANG UNIVERSITY), Seoul (KR); INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 1241 days.

This patent is subject to a terminal disclaimer.

(21) Appl. No.: 17/617,177

(22) PCT Filed: May 8, 2020

(86) PCT No.: PCT/KR2020/006064

§ 371 (c)(1),
(2) Date: Dec. 7, 2021

(87) PCT Pub. No.: WO2020/246717

PCT Pub. Date: Dec. 10, 2020

(65) Prior Publication Data

US 2022/0348927 A1 Nov. 3, 2022

(30) Foreign Application Priority Data

Jun. 7, 2019 (KR) ........................ 10-2019-0067519

(51) Int. Cl.
*C12N 15/113* (2010.01)
*A61P 35/00* (2006.01)

(52) U.S. Cl.
CPC .......... *C12N 15/1137* (2013.01); *A61P 35/00* (2018.01); *C12N 2310/11* (2013.01); *C12N 2310/127* (2013.01); *C12N 2310/14* (2013.01); *C12N 2310/141* (2013.01); *C12N 2310/531* (2013.01)

(58) Field of Classification Search
None
See application file for complete search history.

(56) References Cited

U.S. PATENT DOCUMENTS

2016/0160295 A1* 6/2016 Chinnaiyan .......... C12Q 1/6886 506/9
2016/0271163 A1 9/2016 Marine et al.
2018/0112272 A1 4/2018 Wu et al.

OTHER PUBLICATIONS

Yan (et al. 2010. Squamous cell carcinoma—similarities and differences among anatomical sites. Am. J. Canc. Res. 1[3]:275-300) (Year: 2010).*
Wang (et al. 2016. Long noncoding RNA MALAT1 promotes malignant development of esophageal squamous cell carcinoma by targeting B-catenin via Ezh2. Oncotarget 7[18]:25668-25682) (Year: 2016).*
You (et al. 2019. HERES, a IncRNA that regulates canonical and noncanonical Wnt signaling pathways via interaction with EZH2. PNAS 116[49]:24620-24629) (Year: 2019).*
American Cancer Society ("Cancer Risk and Prevention" and "Esophagus Cancer Causes, Risk Factors, and Prevention". Available online at cancer.org. Accessed on Jun. 11, 2025) (Year: 2025).*
Moffitt Cancer Center ("Types of Squamous Cell Carcinoma". Available online at moffitt.org. Accessed on Jun. 11, 2025) (Year: 2025).*
Vickers (et al. 2000. Effects of RNA secondary structure on cellular antisense activity. Nuc. Acid Res. 28[6]: 1340-134) (Year: 2000).*

(Continued)

*Primary Examiner* — Nancy J Leith
*Assistant Examiner* — Ruth Sophia Arieti
(74) *Attorney, Agent, or Firm* — Sughrue Mion, PLLC

(57) ABSTRACT

The present invention pertains to a pharmaceutical composition for preventing or treating squamous cell carcinoma, the pharmaceutical composition containing a highly expressed lncRNAs in esophageal squamous cell carcinoma (HERES) expression inhibitor. More specifically, the present invention pertains to a pharmaceutical composition which uses a HERES expression inhibitor to reduce the expression of HERES and affect Wnt signaling pathways, and thereby prevent or treat squamous cell carcinoma.

The present inventors discovered that the expression pattern of HERES is related to the onset of squamous cell carcinoma, and found that HERES can be a target for treating squamous cell carcinoma. Accordingly, the pharmaceutical composition according to the present invention was determined to have the effect of inhibiting the proliferation, metastasis, and the like of squamous cell carcinoma by containing the HERES expression inhibitor, and is thus expected to be advantageously used for preventing and treating or ameliorating squamous cell carcinoma.

3 Claims, 18 Drawing Sheets

Specification includes a Sequence Listing.

(56) References Cited

OTHER PUBLICATIONS

Luming Wang , et al., "Long non-coding RNA LINC01296 promotes esophageal squamous cell carcinoma cell proliferation and invasion by epigenetic suppression of KLF2", American Journal of Cancer Research, 2018, pp. 2020-2029, vol. 8, No. 10.
Jun Yu., et al., "Bioinformatics identification of IncRNA biomarkers associated with the progression of esophageal squamous cell carcinoma", Molecular Medicine Reports, May 2019, pp. 5309-5320; vol. 19.
NCBI. GenBank accession No. AC006460.4 , Apr. 2005.
Wen-Jun Shen, et al., "LncRNAs and Esophageal Squamous Cell Carcinoma—Implications for Pathogenesis and Drug Development", Journal of Cancer, 2016, pp. 1258-1264, , vol. 7 http://www.jcancer.org.
International Search Report for PCT/KR2020/006064 dated Sep. 10, 2020.
Written Opinion for PCT/KR2020/006064 dated Sep. 10, 2020.

* cited by examiner

【FIG. 1】
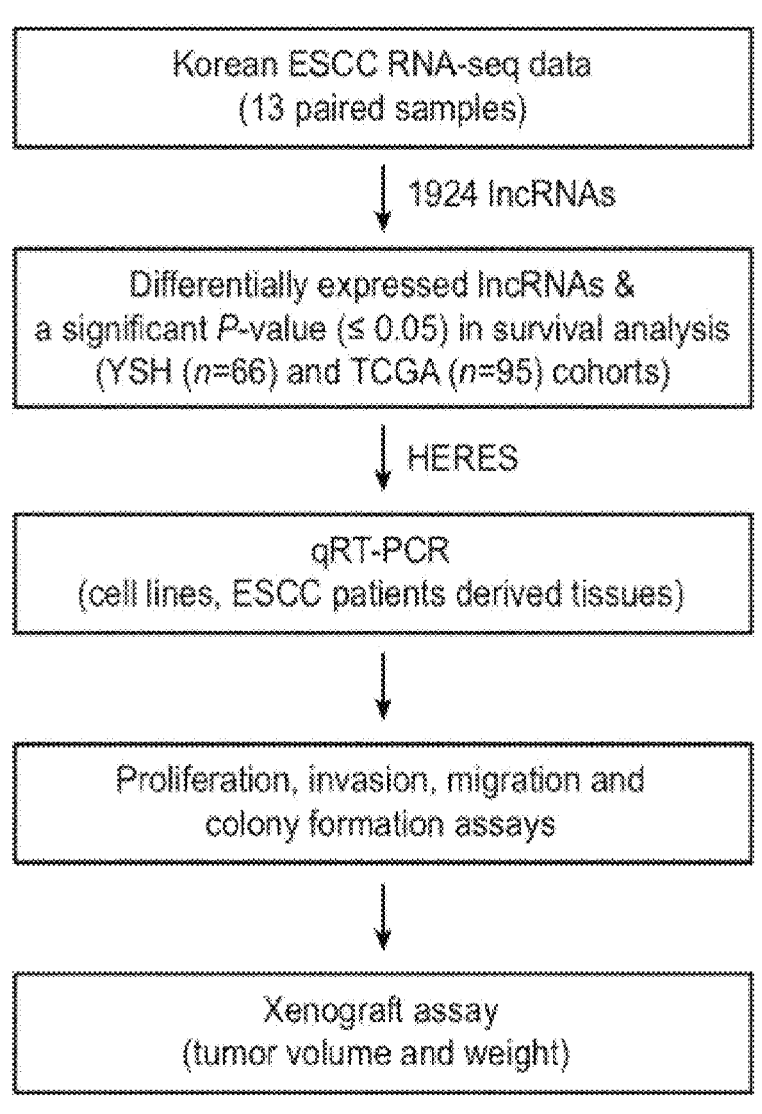

【FIG. 2a】
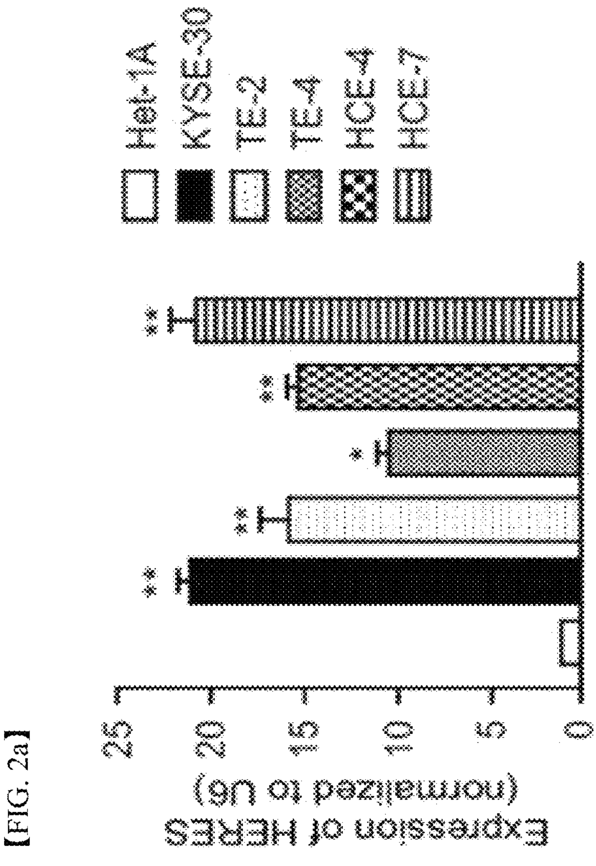

【FIG. 2b】
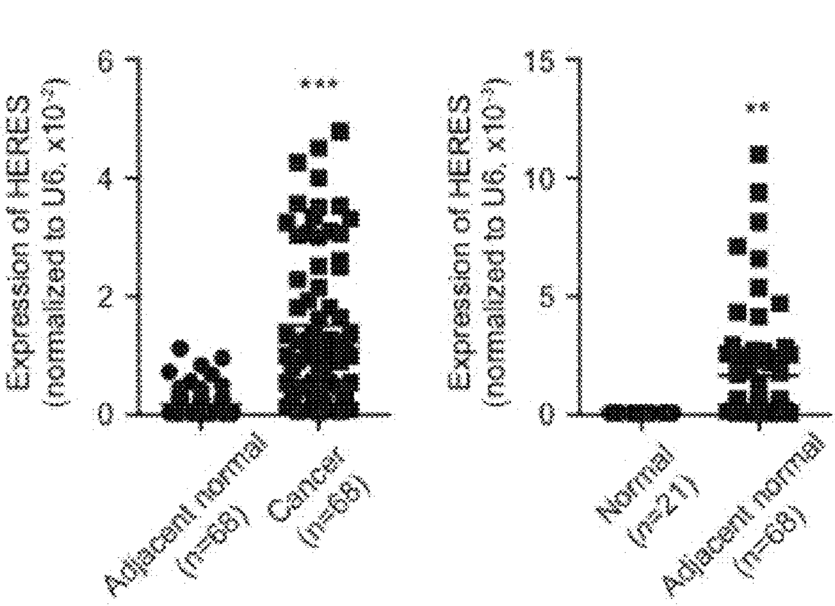

【FIG. 2c】
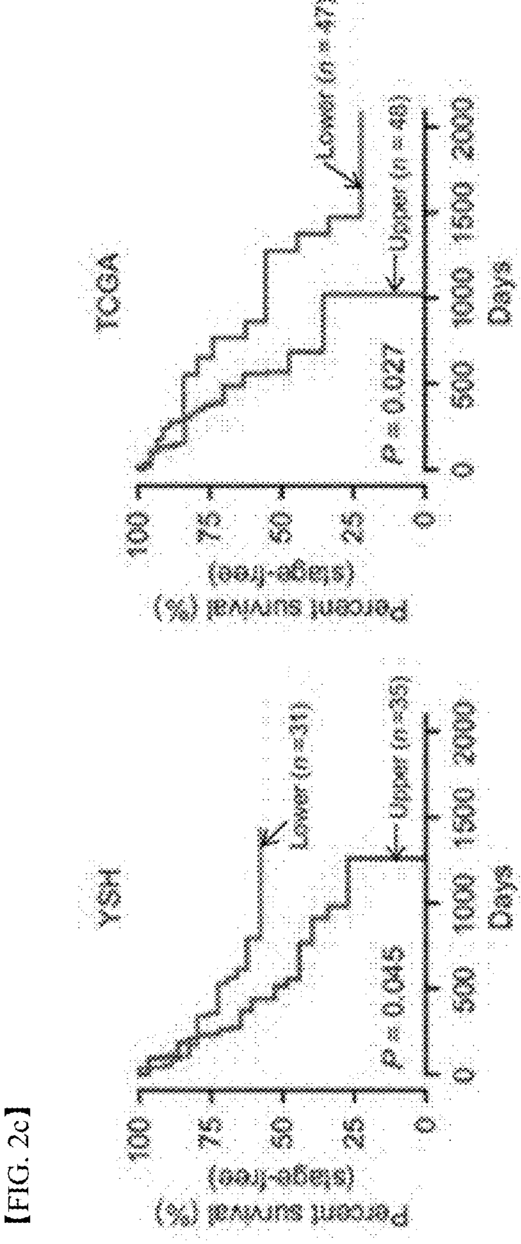

【FIG. 3a】
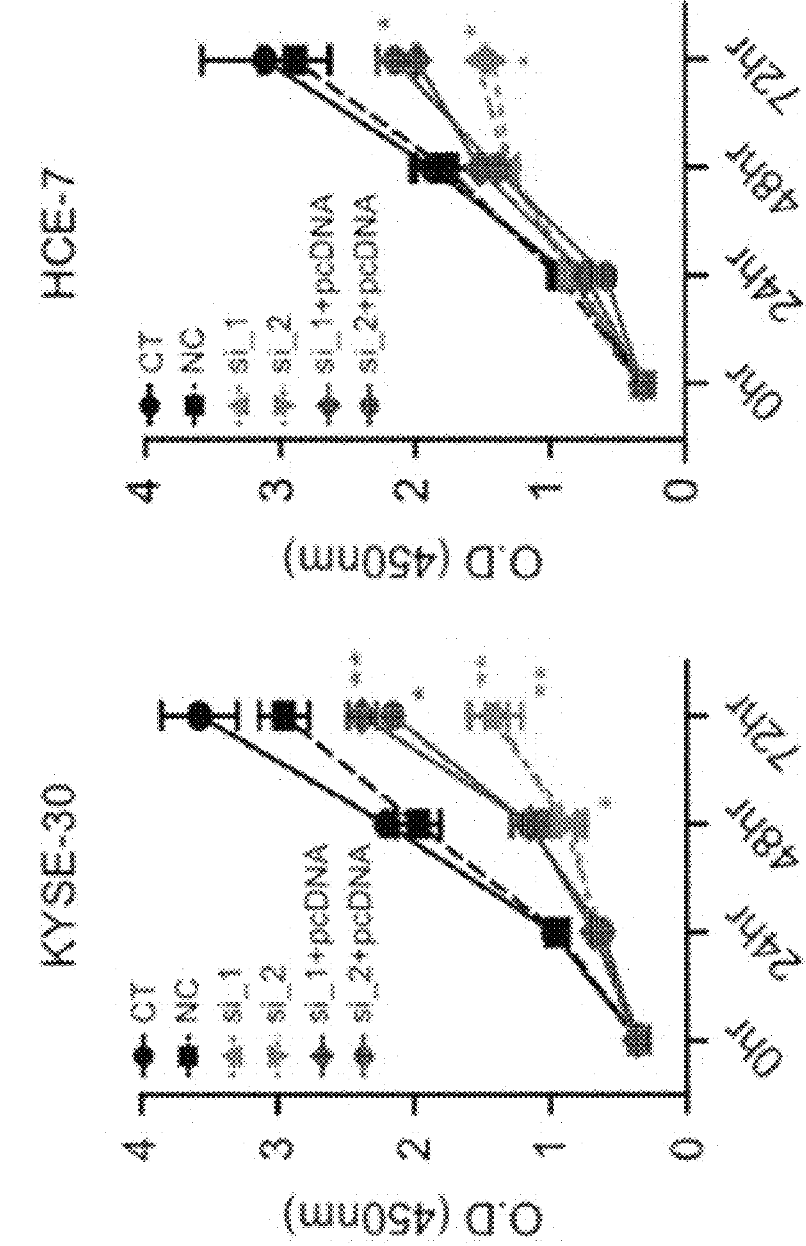

【FIG. 3b】
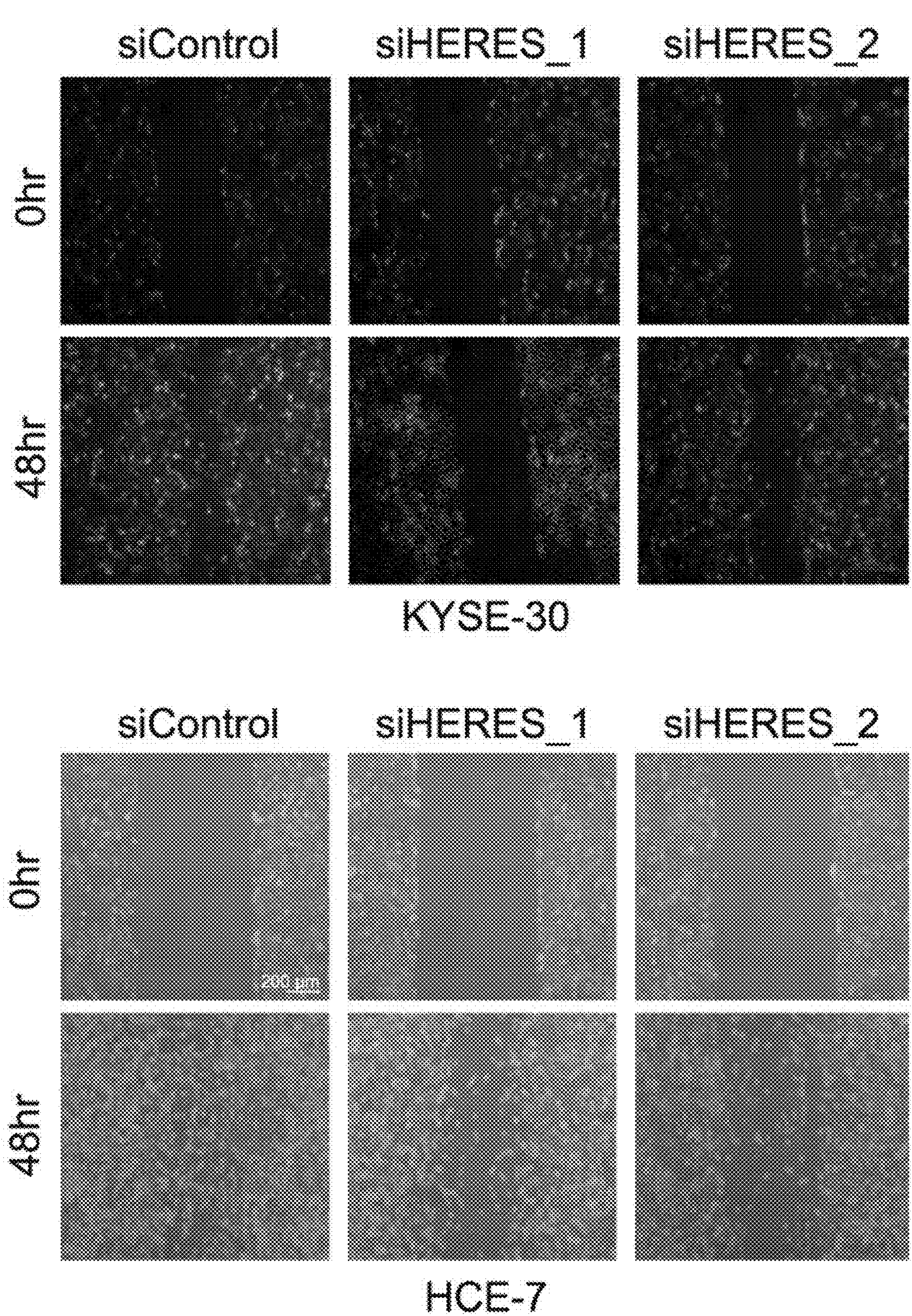

【FIG. 3c】
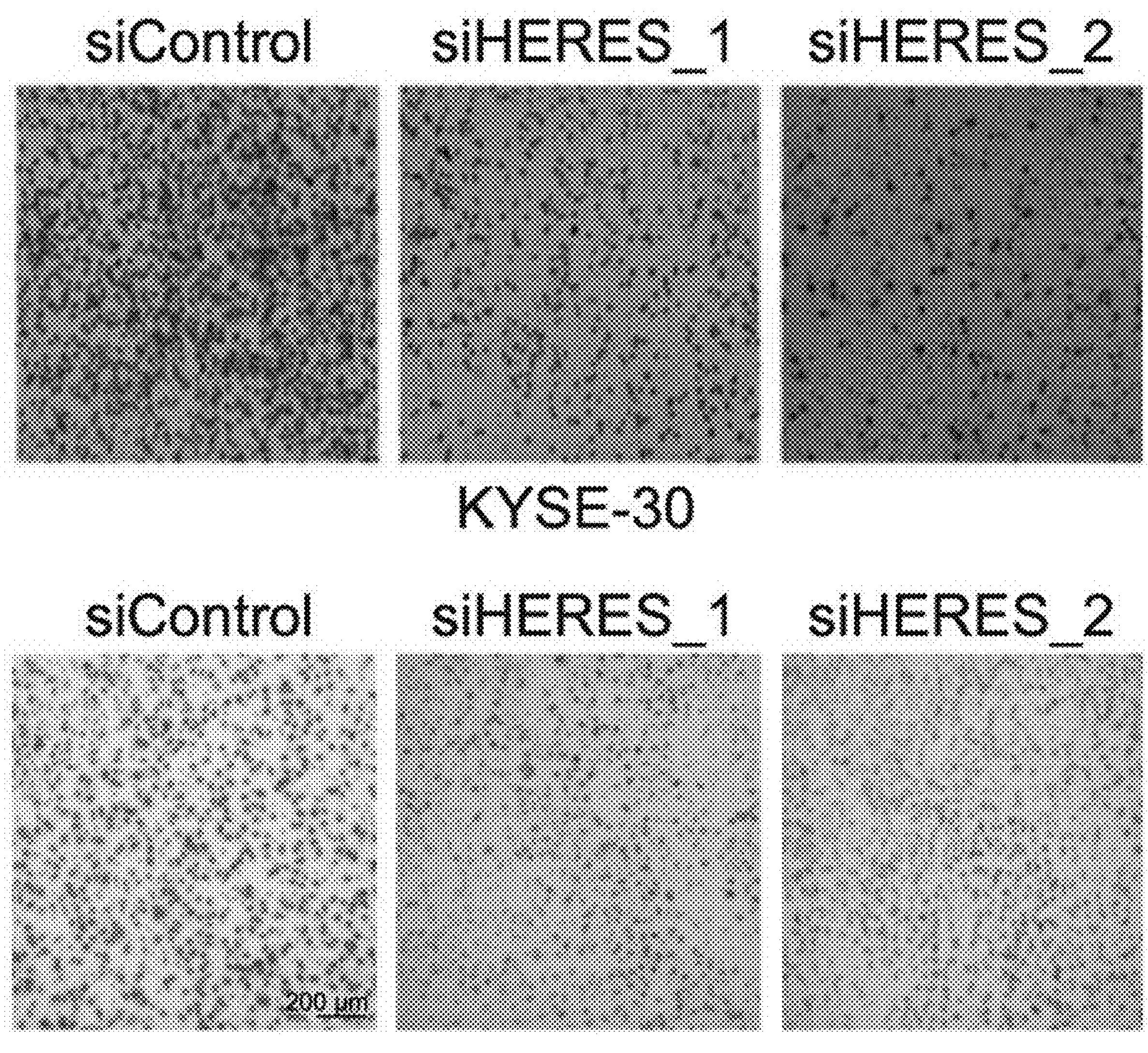

【FIG. 3d】
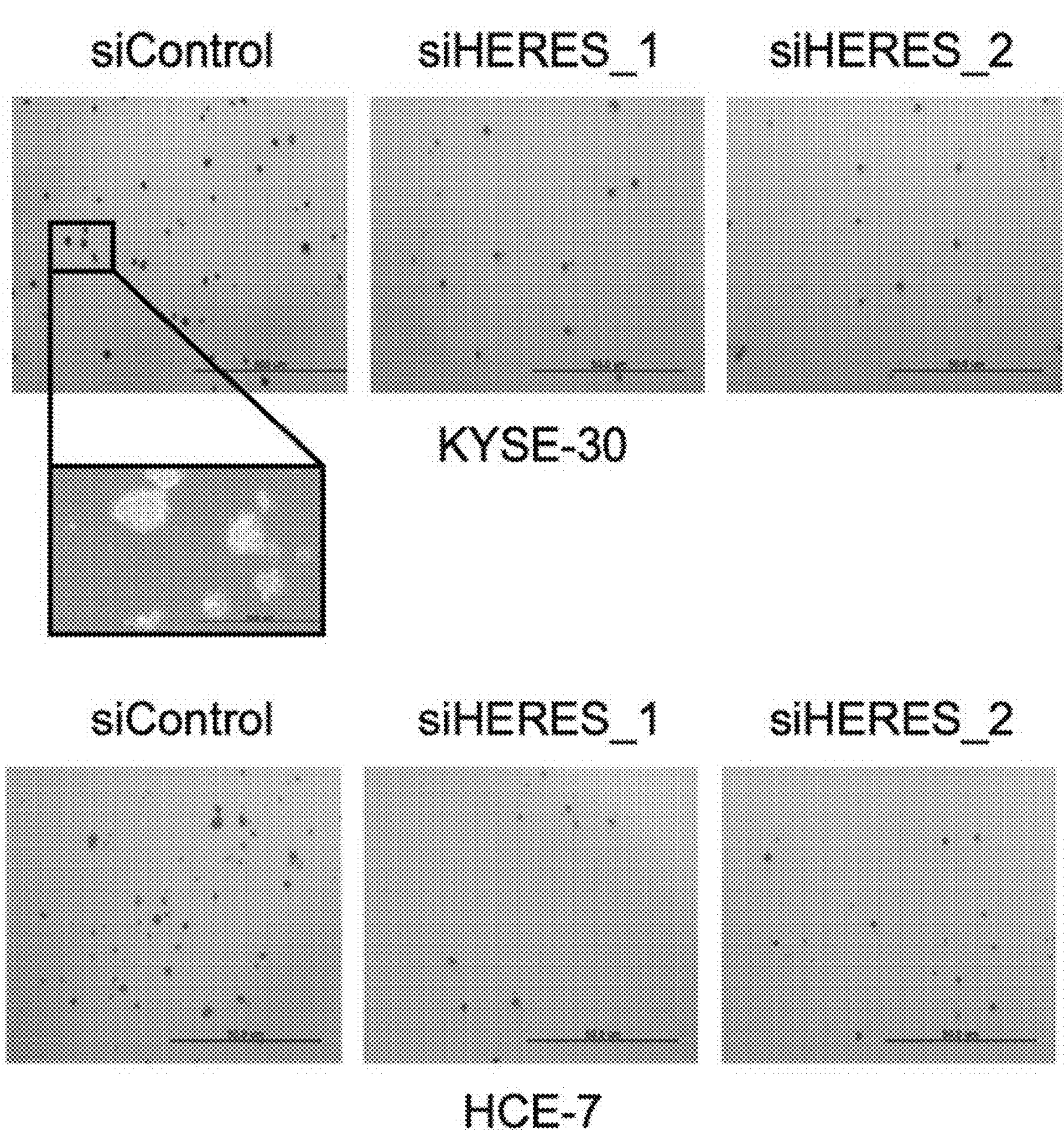

【FIG. 3e】
siControl + — — — —
siHERES_1 — + — + —
siHERES_2 — — + — +
pcDNA-HERES — — — + +
E-cadherin
N-cadherin
Vimentin
β-actin
KYSE-30
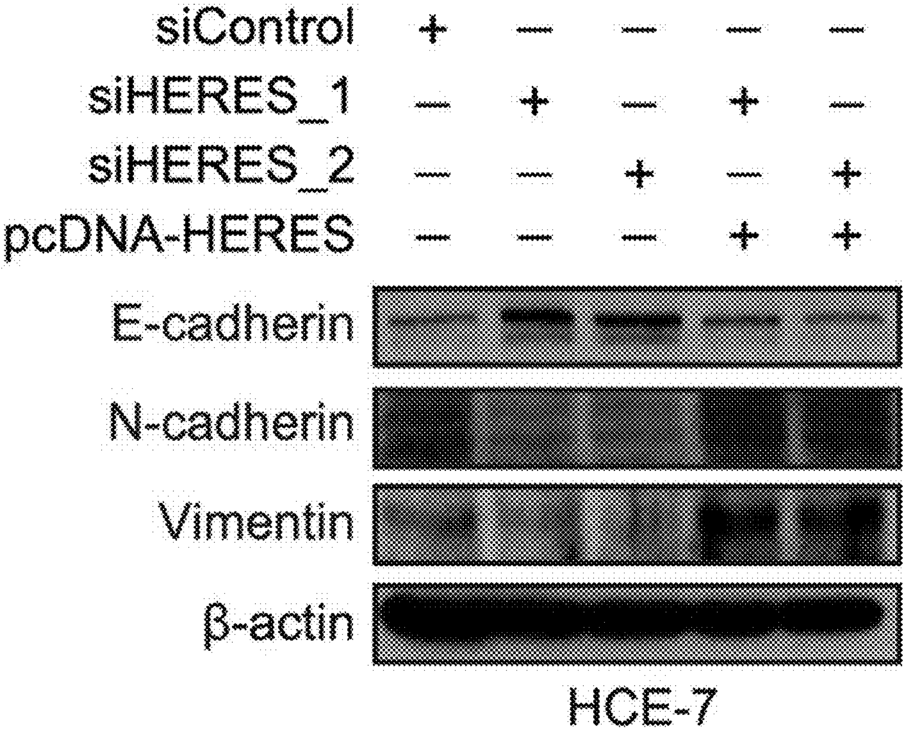

【FIG. 4】
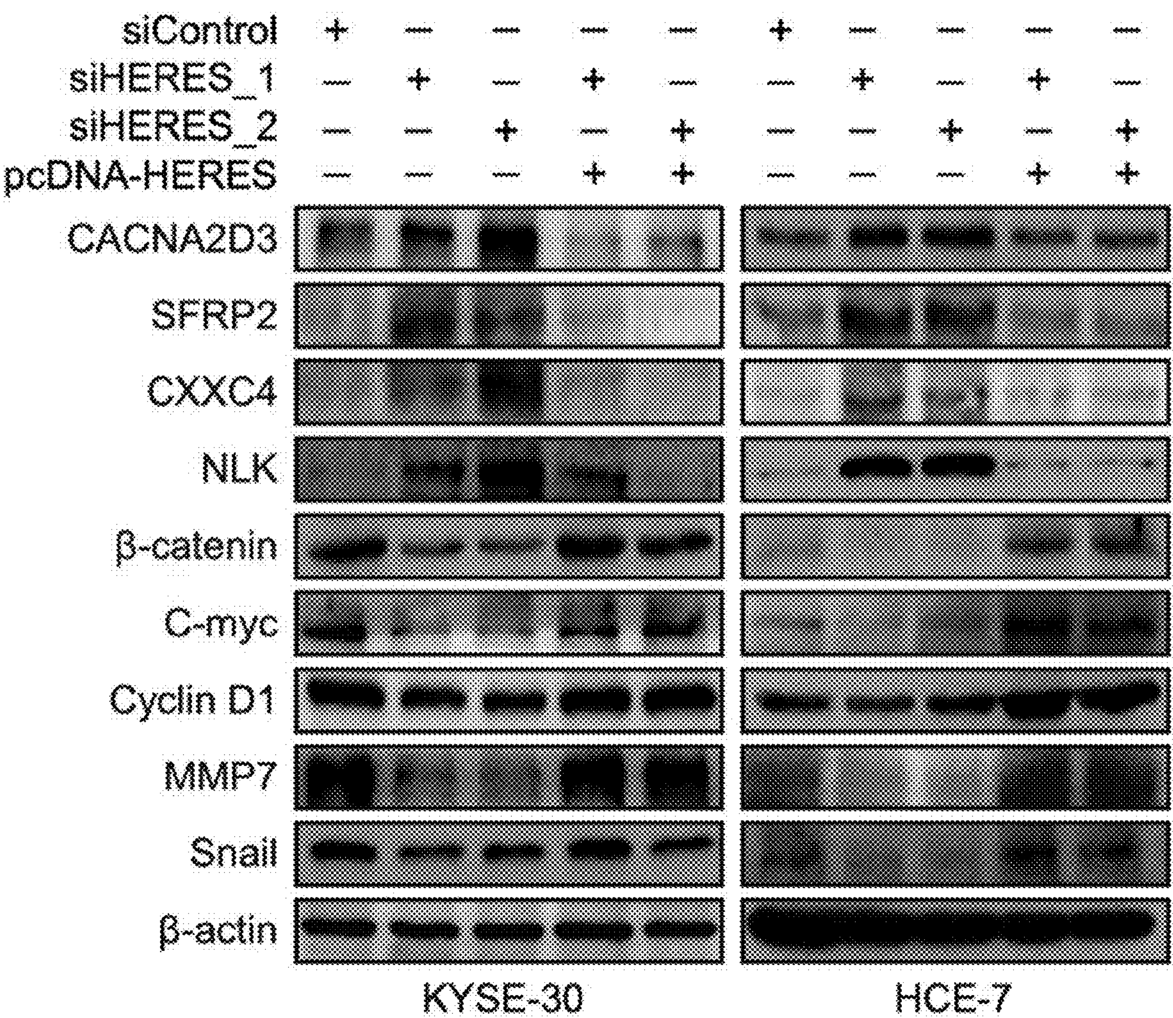

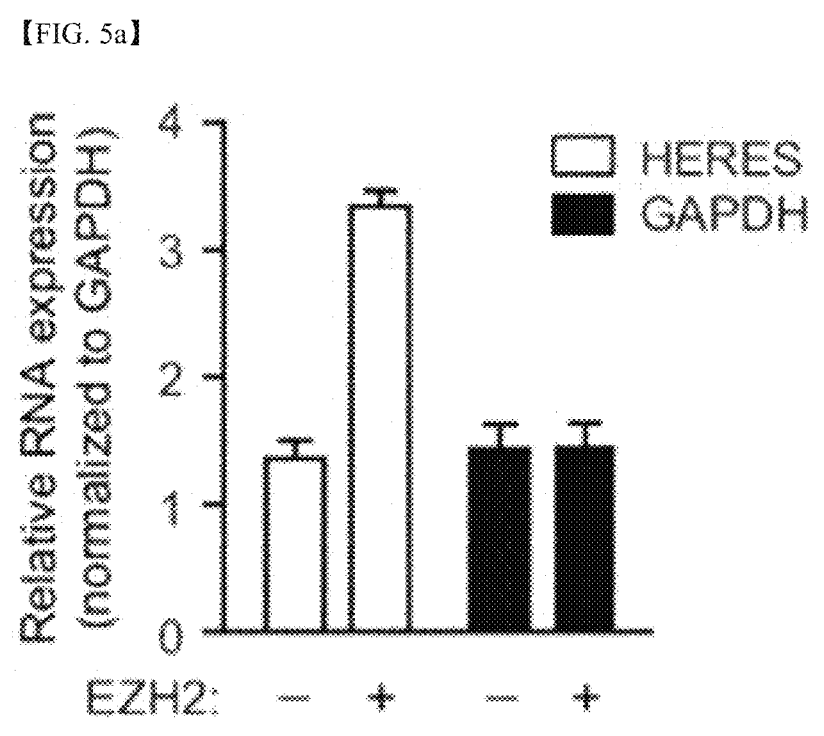

【FIG. 5a】

【FIG. 5b】
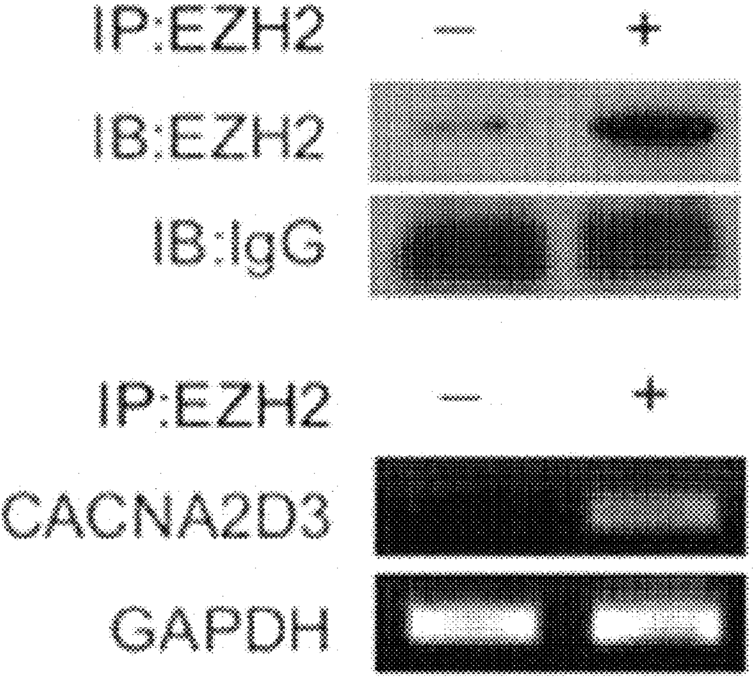

【FIG. 5c】
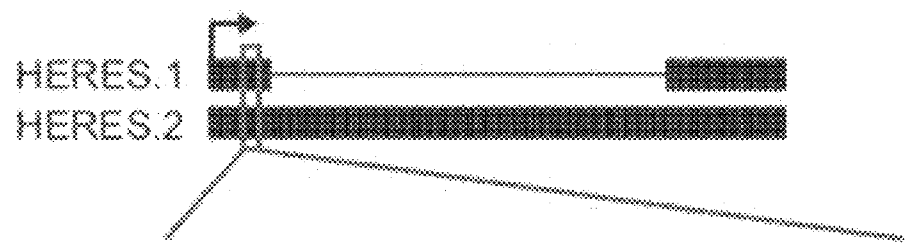

【FIG. 5d】
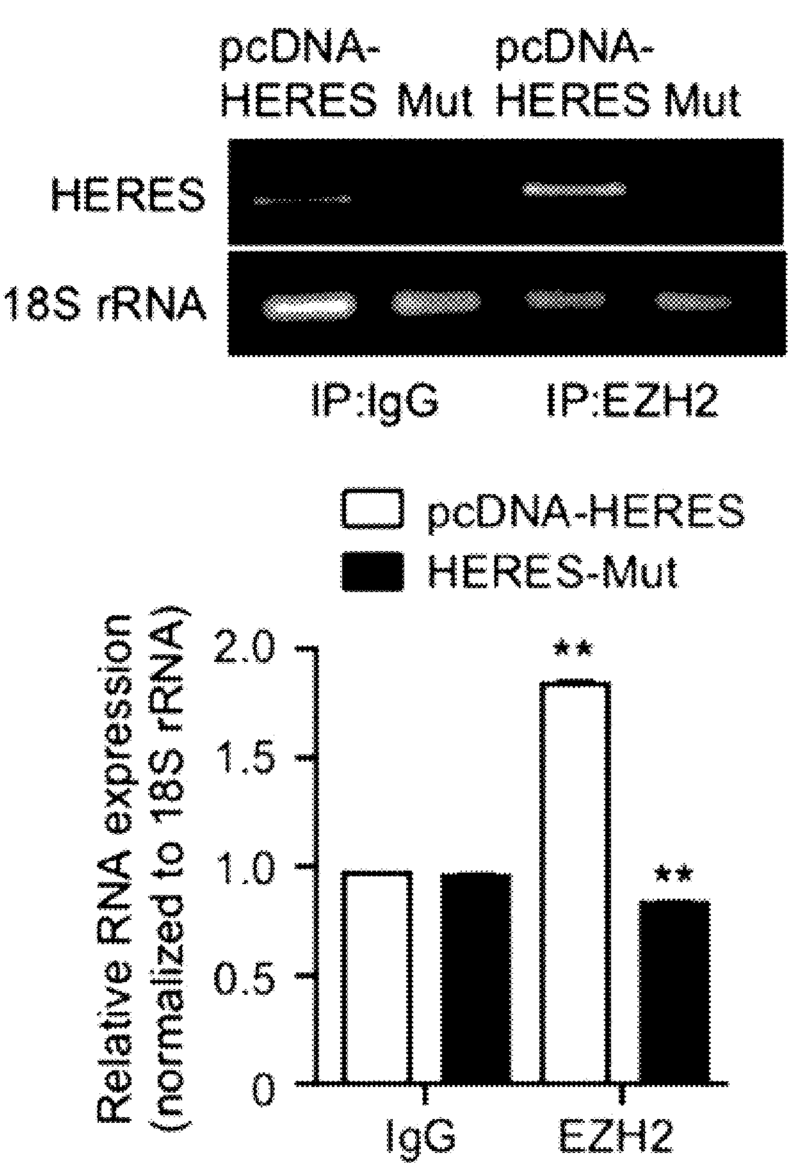

【FIG. 5e】
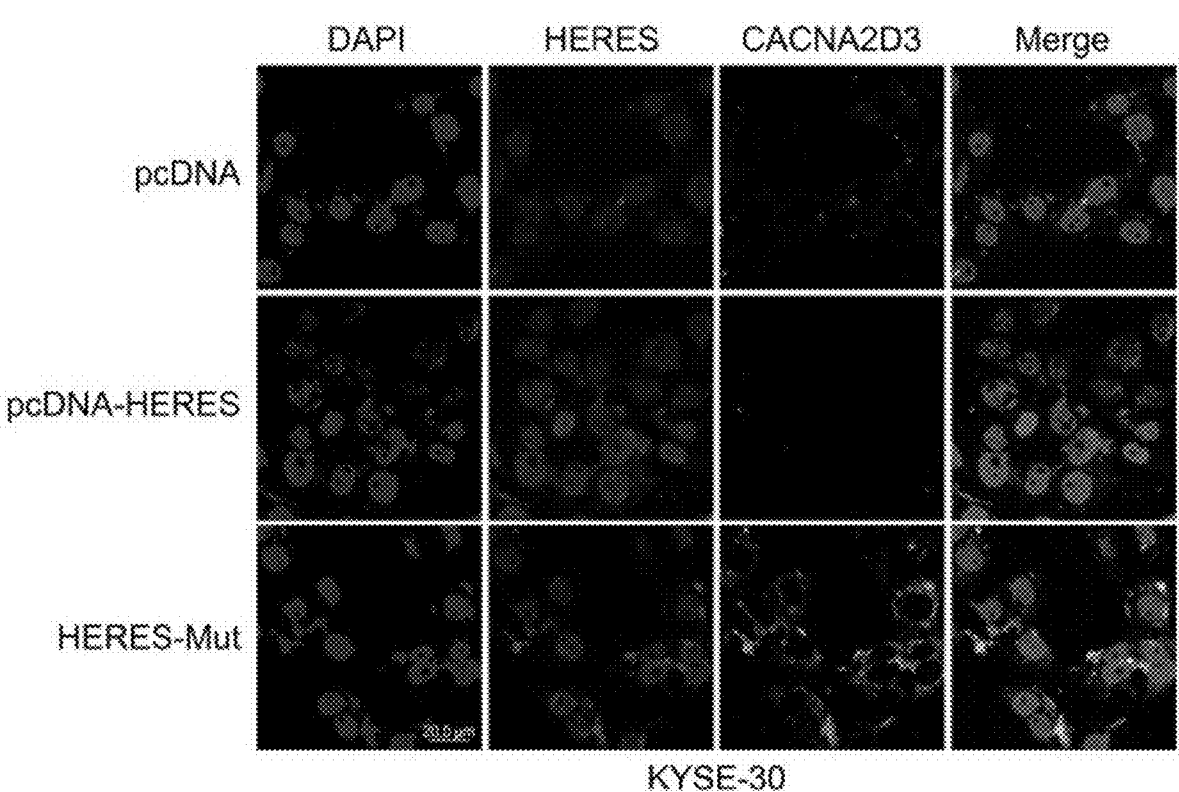

【FIG. 6a】
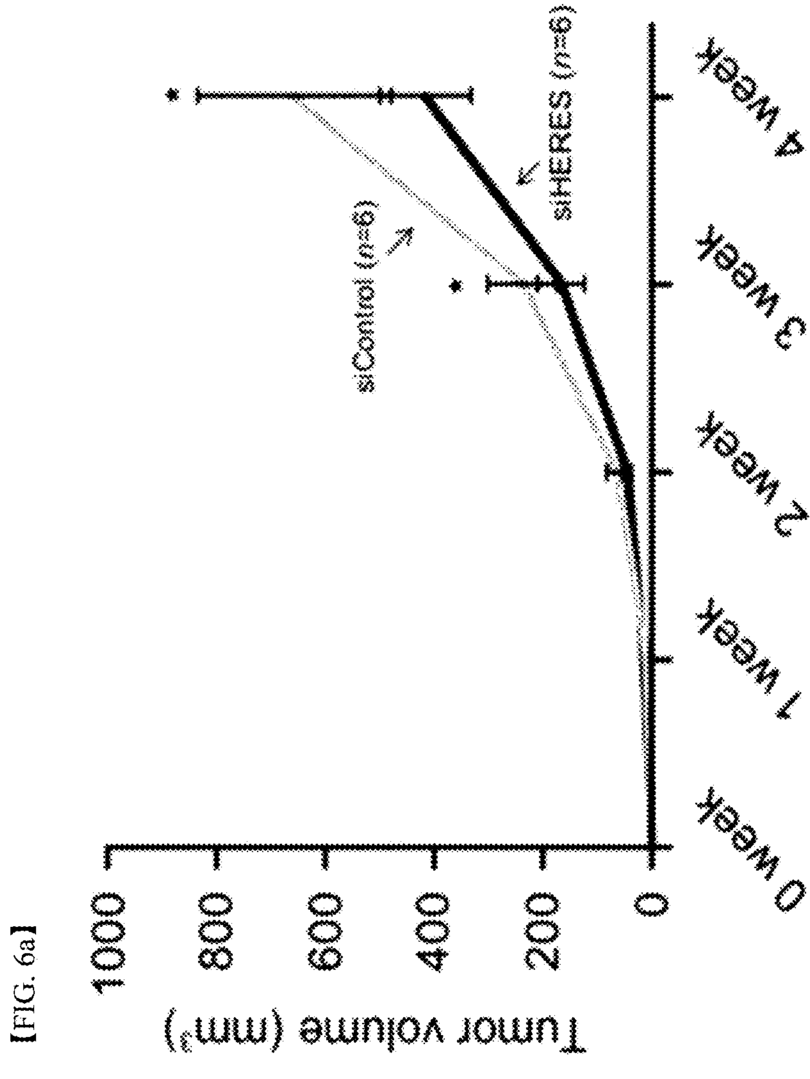

【FIG. 6b】
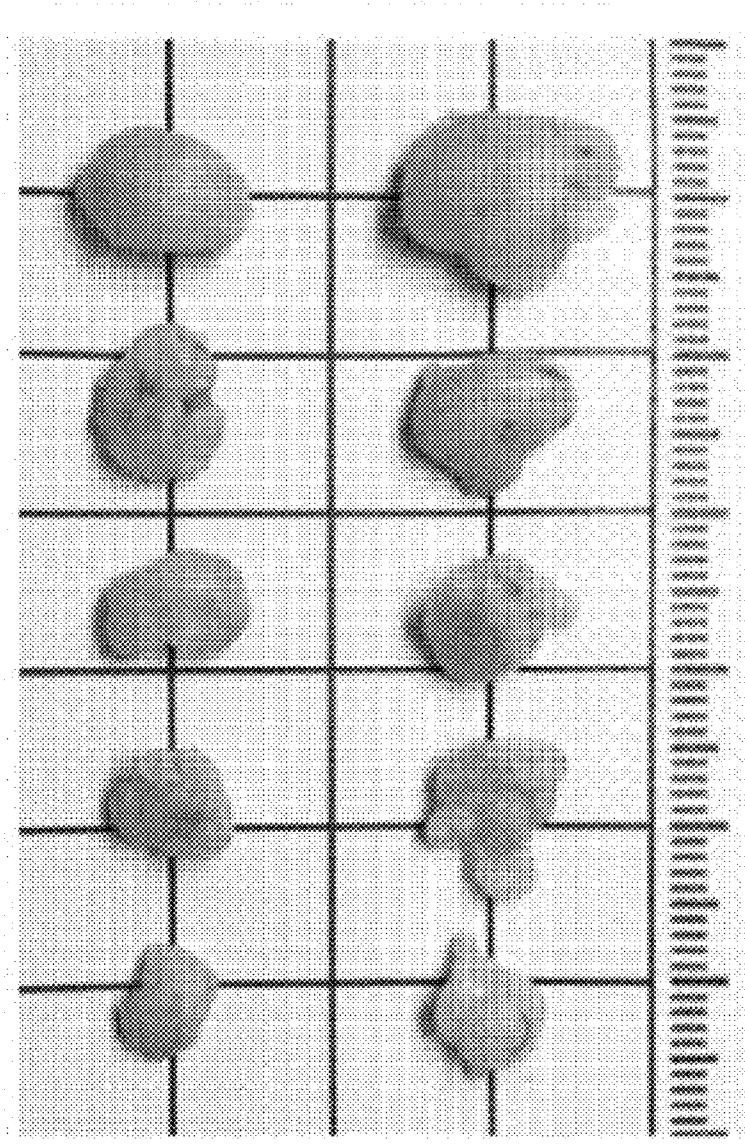

【FIG. 6c】
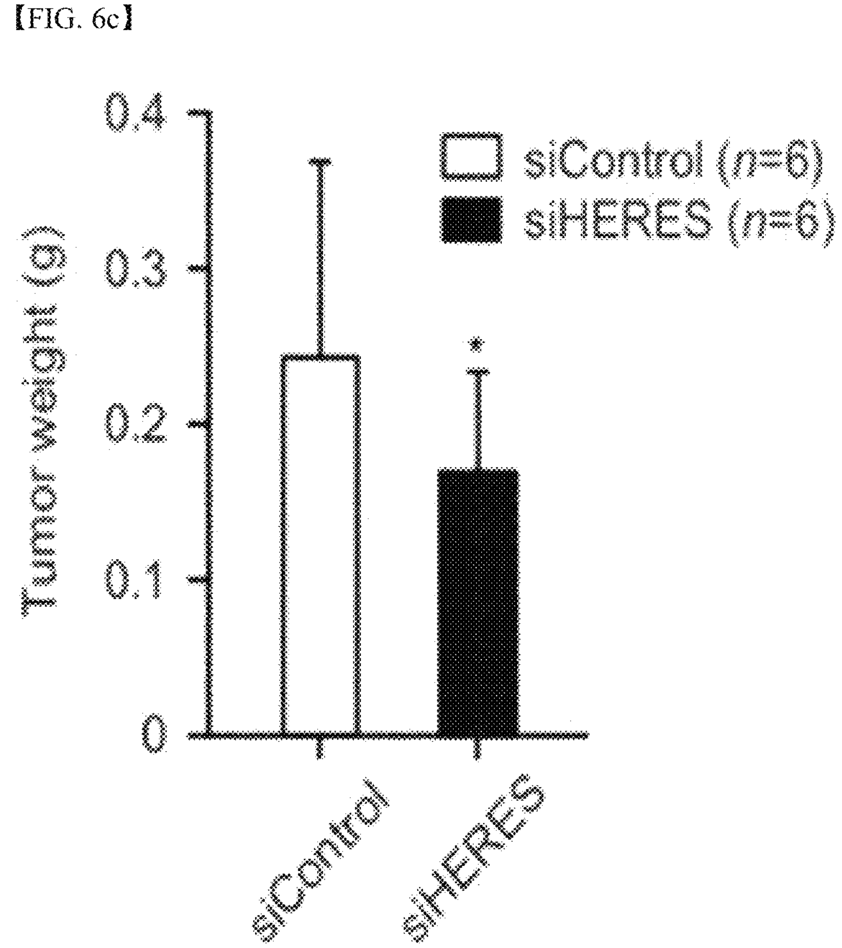

SEQUENCE LISTING

```
<160> NUMBER OF SEQ ID NOS: 9

<210> SEQ ID NO 1
<211> LENGTH: 2160
<212> TYPE: DNA
<213> ORGANISM: Homosapiens

<400> SEQUENCE: 1

ggcaaccagc ttgcgtccgt ttccatgttg tgggagattt gttctttcgc tctttgtggt      60

aaatcttgct actgctcact ctttgagtcc acactgcttt tatgagctgt aacactcacc     120

gggaaggtct gcagcttcaa tcctgaagcc agcgaggcca ccagcccacc gggaggaacg     180

aacaactcca gacgcaccgc cttaagagct gtaacactca ccgcgaaggt ctgcagcttc     240

actcctgagc cagcgagacc acgaacccac cagaagaaag aaactccgaa cacatccgaa     300

caccagaagg aacaaactcc agacgcgcca actgtaacac tcaccgcgag gatccgtggc     360

ttcattcttg aagtcagtga gaccaagaac ccaccaattc cggacacact gtgagtcagg     420

atcagtctta ttatagctaa ttagagcaac cccattgcta aagagtttag agcctgggtc     480

agacttcatg gtagcaaagc aatgttttat tgtaatagtg taattaggaa tgtgtggcaa     540

tattttaacc cctcctccca agagttccac aatgctttct taacatgttt ataaatattt     600
```

-continued

```
gcttttgtgc cattttaggg gagctttccg tacaaacatt tggcttttaa tgagtcatcc    660

acactctgat tcatacccat aagcttcctg ctttgttatc agtgaatatt gggctcagta    720

actgccttac ttttataatt tacatgaatg aatatggaaa aggtggtgga ggtagaaaga    780

catattcagg taaatataaa aacaccctgg tttctttaca agagattgac aaatacggcc    840

caataccta tcatttaaaa aaatagctgc tgccccactc ctgtgccaaa atctgctcca    900

agggatccta tcctagtcag aaggctgtac tctgaatgct gatattagct acaacaccaa    960

ggcttcccac tatacaaact ggatcctcaa agtcatccac accaaatgaa ctctctattc   1020

tttctcccag tagcctgaga actgggttta ccagccttgg cccttccttt ccttctagcc   1080

tcaaaacagg atgggaacag agtctttggc tgtgagaatg ggctcaataa caaaataaag   1140

atgacagaag agtcagtgac ttcaatgaca gagcgataga aattaccaat ataaacggag   1200

agaaaagaga ttttttaaaa atgaacaaat ccccaaggac ctgtgagaca ataactgtgt   1260

taggttttct aaacttacaa gtgtttttat ttatatatgg taagcaacta tgcattattt   1320

gtgtcagaat tattttttgt atatatttaa ggtatacaac atgatgtctc aacatactta   1380

tatgtagtga aatggttact acagtcacca cacttattgt ctcacaggtt attgtcttca   1440

gaaggagagt aaaaagaatg ctgggtagaa gaaatacctg aagaaataat ggcccaacct   1500

caaatttggt gaaagacata aacttacaga ttcaagaaac tgagtgttcc ccaaacagaa   1560

taaactttaa agaatccaca ctcaaacaca tcataatcaa acttctgaaa actaacaaca   1620

aagaaaaact taaaatcagc aagagagaaa ccacacatta tcaactgatg aaaagtgact   1680

caagtgacag cagatttata atcagaaact tgaaggacag aaggaagagg caaaacattt   1740

tgaaagccct aaaaggaaag aactgtcaac ccagaattcg acatccagta aaaatatccg   1800

tcaagaatga atatgaagga aagctaagaa tgaatatatc ttctatttct ttgctaaatt   1860

tttctacttt ttcatttgat gtaagagtgt ttataagtgc ttatggagca tttttatgat   1920

agttggttta caatccttgt ctgagagtag ctatgtgaga tgacgtatat agtaaatggt   1980

gactgtagta accatttcac tacatataag tatgtcaaaa catgttgtac accttaaata   2040

tacacaaaaa atagctctga cacaaaaaat gcatagttgt tattaccatg tataaataaa   2100

aatacttgta agtttagaaa ataaaatcat tgtctgataa ttatctaaat aataaagtcc   2160
```

<210> SEQ ID NO 2
<211> LENGTH: 6675
<212> TYPE: DNA
<213> ORGANISM: Homo sapiens

<400> SEQUENCE: 2

```
ggcaaccagc ttgcgtccgt ttccatgttg tgggagattt gttctttcgc tctttgtggt     60

aaatcttgct actgctcact ctttgagtcc acactgcttt tatgagctgt aacactcacc    120

gggaaggtct gcagcttcaa tcctgaagcc agcgaggcca ccagcccacc gggaggaacg    180

aacaactcca gacgcaccgc cttaagagct gtaacactca ccgcgaaggt ctgcagcttc    240

actcctgagc cagcgagacc acgaacccac cagaagaaag aaactccgaa cacatccgaa    300

caccagaagg aacaaactcc agacgcgcca actgtaacac tcaccgcgag gatccgtggc    360

ttcattcttg aagtcagtga gaccaagaac ccaccaattc cggacacact gtgagtcagg    420

atcagtctta ttatagctaa ttagagcaac cccattgcta aagagtttag agcctgggtc    480

agacttcatg gtagcaaagc aatgttttat tgtaatagtg taattaggaa tgtgtggcaa    540

tattttaacc cctcctccca agagttccac aatgctttct taacatgttt ataaatattt    600
```

-continued

```
gcttttgtgc cattttaggg gagctttccg tacaaacatt tggcttttaa tgagtcatcc    660
acactctgat tcatacccat aagcttcctg ctttgttatc agtgaatatt gggctcagta    720
actgccttac ttttataatt tacatgaatg aatatggaaa aggtggtgga ggtagaaaga    780
catattcagg taaatataaa aacaccctgg tttctttaca agagattgac aaatacggcc    840
caataccta tcatttaaag taagtgccag aattgtgatg gatttgtgtt tggccttaaa    900
aaaaaataaa aataaaaata aaaacaaaaa cacttggata attctacctg atgttacatt    960
tttctttttt tttttctttt cttttttttt ttttttttt gagatggagt tttcctctgt   1020
cacccaggct ggagtgcagt gacgtgacct cagctcgctg caacctctgc ctcccagatt   1080
caagcaattc tctctcaaat tgctcagaag ctgagcaatt ctgcctcagc ttcccaaata   1140
gctgggatta caggtgcgtg ccaccaggct cagctaattt ttgtattttt agtagagatg   1200
gggtttcacc atgttggcca ggctggtctt gaactcccga cctcaggtga tacgcccgcc   1260
tcggcctccc aaagtgctgg gattacaggc atgagccact gcgcccagcc tgatgttcca   1320
tttttctaat caccaagtgt atttattagc taagggtatc ccagaaatta aattaccaac   1380
ataaaatttt acttgtgcta ttataattta gctattaaat cctaaaatta tcaactgaaa   1440
gctactggaa aaataaatac ttctctttct tttctccata ttgaaagtaa agagaatgag   1500
gatccttagc taagatttta attaaatctt ttctgagcca gaattgcaaa gcttttcttt   1560
gtataaataa ggactcgagt tataaagcat agaactagca atgagtctat cttggtccat   1620
ttggattgct ataaaggagt acctgaggct gggtaattta taaagaaaag acgtttattc   1680
gacacatgat tctgcaggat gtacaagaag catggcacca gcatctgctc ttggtgaaaa   1740
cttcaggtgg ctttgactcc tggtggaaga agggaagtct agcttgtgca gagctcccat   1800
ggccagagaa ggaagggggg tttgaggagg tgccaggctc tttgaataga gcgagaactc   1860
actcattacc aagagaaggc accaagccat tcatgaggga tacacccctg tgacccaaac   1920
cttgcccccc ttccaacatt ggggcttaaa tttcaatgtg atgtttaggg gtacaaacat   1980
ccaaaccaca gcagagaaat acagagttct gtatttctat tcccaaaggg caaaatttgg   2040
gaggtgaatg ggtctatatg tgtgttgggg ggaagaagtt aatatgaaga aaagaaacta   2100
aagtgcttta cataataatg agaattacag attaaaaaat ctgtaatctt tccctaaaaa   2160
gggaaagaag taccatgcaa attatgaggt aagtagacta tatgacttat ttatttttat   2220
taggttagag caagaattgc aaactcaagg tcctgactcc ttgaattgca ctctatggac   2280
ccagtcatac ttcatttgca tattatatat taaatgcttt ggcatgatct ttgctccccc   2340
ttacatcctc aaaacactct ttttccattt ttcttaaaat atatgttcct ctttgtctat   2400
atttttatttt tccaactttg aaaaggactt acacataaaa atggtatcac tttcttctta   2460
actgtaagaa aaatggtctc agccatacat tgatgaatgg cagctgtcat tcagcctcag   2520
tgtgaaggag acaacaatga gtggtgagga ctgtaataaa atggaaagca catgcccatc   2580
caaaagtgag cattcacttc taggaactag taaaaatggt aatagccaga tctttctatt   2640
ttttcacaag aagcctgaaa gtatttaaat attttatgac taattcaaat gctttaaaaa   2700
taagcaattt gattctagga ggccaaacta gttgctatct atgatttaaa ccatagtgtc   2760
tttcagaatt aatgtatgtc cttggcgggt gtgtgtgtgt gtgtgtgtgt gtgatcccaa   2820
aacaccaata attaccagtg aaaaatttag gagattaaat atgtgtactt taatccacat   2880
tgggggaaga gagagatata aaaggtgctg agaaccttga agtggtgccc ctcctgatct   2940
```

```
gccttctacc tcttcaacat acgtgctgtg caccatgaaa gacttgaagt gcaatggcaa   3000
tctgtgatcc tttgtggaaa cctttcccta atttgcccca gagtgaatgt ttcacacttg   3060
gattcacatt tgctgagaga ggcggaaaaa tcttagggac aattagaaca ataataacaa   3120
cattcatatt attattcaat gacagcaaca ttcatattca ttctttcatt cagcaaatat   3180
ttattgcaca cttgctatgt gctagaacta taaaatggca atgatgtgtt aggtaatttg   3240
taatcatggg gaaaaaatca gttagggaaa gacaaaactg ccttccctta tagagattat   3300
attcattgag gagacaaata ataaataaaa tgaatagtgt aacataggtt agatagtgac   3360
aagtgctatg gagaaaaaga aagtaggaaa gggtcatttc tctggtttcc tgatgtgtaa   3420
ttggaataga tatccttggt agctggtaga atctctgcag tgattccttg tactgtgggg   3480
taaaagctat gttagcaggg gagaccaaga ggaatagctg aaacaaaatt cactttctca   3540
gtaagatagt aaataagaaa gtgatattgc atcctgggaa acatggccga gattagtgct   3600
tctctttaag acctaaagga tgcagagtga tggccctcac tcatcctcat ttaattcacc   3660
tgtcaggccc ttgcaaaaat tggtctgatc ctgggggata ataaactcaa ccaaatagtt   3720
gccccaattg cttttgttat gcgagatata tctttgctag aacaaactga ttaacctggc   3780
ctcaggtacc ttgcattgat tggcaaatgt attcatttct attcctgtaa agaaagagaa   3840
acaaaagcac gggaatgaca cagactttta cagcactgag cagggctaat tctcatgccc   3900
tctgtcataa tataacctaa agggacttgg actgtctgga tactccgcac atcaacacca   3960
taacccacta tactgatgat atcatgtgtg atggttttca aatatgcaca caaatttctg   4020
attcttcttt cttcaagagg tggagcttaa ttccccttca attgagggtg agtcgggcat   4080
agtgacttgc ttctaattaa taaaatattg cagaagtgat gatgtggttt ttctaagaca   4140
ctgcaacttc ctttccttgc tctctcttga ataacatgct ctgaaggaaa tcaggtacta   4200
tgtgatgagg acattcaagc aatcctaggg agagattcat gtagaaaaga actaaggcct   4260
cctgccaaaa gccatttgag tcagccctct tggaagtaaa ccctctaccc ctagtaaagc   4320
cttcggatga ctgcagccct gggcagcatc ttgactgcaa actcatgaga gaccctgagc   4380
cacaatcacc cagctaagcc actcttaaat tcctgtccta tactgtgaga taataaatgt   4440
ttactggttt cagctgaaag gtgacagagt gggagtcatg tcaccatctc tggctgtaca   4500
cggaagaatt acagtgagtg acctttaaca caacccctta gtgctccttc ggtacccagt   4560
aaatgagggt tatcatacaa ctatgattat agagcaatag atctggctta ttcatgagac   4620
acttctgagc agtcataaat taaagcatgc atgcaaaagc ccaagatatg ccgttaacaa   4680
cactggaacc agacctcggt tttctcactt tattatctgt tctcctcttc tttggtttct   4740
ttttattttg tttttttcca tcattgaatg atggtgaagt taataatgga aaagagggag   4800
ggaagaagag aagaaaggaa gttgaatata tgaaggacca aagagaatat taccttcctc   4860
cttctcgggt gtgcttagac acaaaaccta acatccaaat aaaccaaggt gtcatttgga   4920
tctctaatgg agattgccaa gagttctgta tgagacagat tcctattaaa gtctcagaac   4980
acgttctgtg caagatcatc tctggagagc atatatgttg ggaaaccctt ttccctctgc   5040
cttccctaaa tttggtctgg aacactgttt tggggtccac acatatcctt caacccaaca   5100
caatctcaac acaagaagag atcagggtaa atggggatca ggaaggaata tgtatccttc   5160
ttccagtcat gaatgaactt agatatcagg gggacaaatt tctgagtgtt atttctccat   5220
ggcttcccct gatgtggcct aagtgggtga ggaggcattt ttcccagccc ttatcaccca   5280
agtctttcta ttctggcccc tcagatagag acttggtaat acatcacttt tgttttggct   5340
```

gccctgcctg acccacctct cctctttcta acagaaaata gctgctgccc cactcctgtg 5400
ccaaaatctg ctccaaggga tcctatccta gtcagaaggc tgtactctga atgctgatat 5460
tagctacaac accaaggctt cccactatac aaactggatc ctcaaagtca tccacaccaa 5520
atgaactctc tattctttct cccagtagcc tgagaactgg gtttaccagc cttggccctt 5580
cctttccttc tagcctcaaa acaggatggg aacagagtct ttggctgtga gaatgggctc 5640
aataacaaaa taaagatgac agaagagtca gtgacttcaa tgacagagcg atagaaatta 5700
ccaatataaa cggagagaaa agagattttt taaaaatgaa caaatcccca aggacctgtg 5760
agacaataac tgtgttaggt tttctaaact tacaagtgtt tttatttata tatggtaagc 5820
aactatgcat tatttgtgtc agaattattt tttgtatata tttaaggtat acaacatgat 5880
gtctcaacat acttatatgt agtgaaatgg ttactacagt caccacactt attgtctcac 5940
aggttattgt cttcagaagg agagtaaaaa gaatgctggg tagaagaaat acctgaagaa 6000
ataatggccc aacctcaaat ttggtgaaag acataaactt acagattcaa gaaactgagt 6060
gttccccaaa cagaataaac tttaaagaat ccacactcaa acacatcata atcaaacttc 6120
tgaaaactaa caacaaagaa aaacttaaaa tcagcaagag agaaaccaca cattatcaac 6180
tgatgaaaag tgactcaagt gacagcagat ttataatcag aaacttgaag gacagaagga 6240
agaggcaaaa cattttgaaa gccctaaaag gaaagaactg tcaacccaga attcgacatc 6300
cagtaaaaat atccgtcaag aatgaatatg aaggaaagct aagaatgaat atatcttcta 6360
tttctttgct aaatttttct actttttcat ttgatgtaag agtgtttata agtgcttatg 6420
gagcattttt atgatagttg gtttacaatc cttgtctgag agtagctatg tgagatgacg 6480
tatatagtaa atggtgactg tagtaaccat ttcactacat ataagtatgt caaaacatgt 6540
tgtacacctt aaatatacac aaaaaatagc tctgacacaa aaaatgcata gttgttatta 6600
ccatgtataa ataaaaatac ttgtaagttt agaaaataaa atcattgtct gataattatc 6660
taaataataa agtcc 6675

<210> SEQ ID NO 3
<211> LENGTH: 6675
<212> TYPE: DNA
<213> ORGANISM: Homo sapiens

<400> SEQUENCE: 3
ggcaaccagc ttgcgtccgt ttccatgttg tgggagattt gttctttcgc tctttgtggt 60
aaatcttgct actgctcact ctttgagtcc acactgcttt tatgagctgt aacactcacc 120
gggaaggtct gcagcttcaa tcctgaagcc agcgaggcca ccagcccacc gggaggaacg 180
aacaactcca gacgcaccgc cttaagagct gtaacactca ccgcgaaggt ctgcagcttc 240
actcctgagc cagcgagacc acgaacccac cagaagaaag aaactccgaa cacatccgaa 300
caccagaagg aacaaactcc agacgcgcca actgtaacac tcaccgcgag gatccgtggc 360
ttcattcttg aagtcagtga gaccaagaac ccaccaattc cggacacact gtgagtcagg 420
atcagtctta ttatagctaa ttagagcaac cccattgcta aagagtttag agcctgggtc 480
agacttcatg gtagcaaagc aatgttttat tgtaatagtg taattaggaa tgtgtggcaa 540
tattttaacc cctcctccca agagttccac aatgctttct taacatgttt ataaatattt 600
gcttttgtgc cattttaggg gagctttccg tacaaacatt tggcttttaa tgagtcatcc 660
acactctgat tcatacccat aagcttcctg ctttgttatc agtgaatatt gggctcagta 720

-continued

```
actgccttac ttttataatt tacatgaatg aatatggaaa aggtggtgga ggtagaaaga    780
catattcagg taaatataaa aacaccctgg tttctttaca agagattgac aaatacggcc    840
caataccta tcatttaaag taagtgccag aattgtgatg gatttgtgtt tggccttaaa    900
aaaaaataaa aataaaaata aaaacaaaaa cacttggata attctacctg atgttacatt    960
tttcttttt tttttctttt cttttttttt ttttttttt gagatggagt tttcctctgt   1020
cacccaggct ggagtgcagt gacgtgacct cagctcgctg caacctctgc ctcccagatt   1080
caagcaattc tctctcaaat tgctcagaag ctgagcaatt ctgcctcagc ttcccaaata   1140
gctgggatta caggtgcgtg ccaccaggct cagctaattt ttgtattttt agtagagatg   1200
gggtttcacc atgttggcca ggctggtctt gaactcccga cctcaggtga tacgcccgcc   1260
tcggcctccc aaagtgctgg gattacaggc atgagccact gcgcccagcc tgatgttcca   1320
tttttctaat caccaagtgt atttattagc taagggtatc ccagaaatta aattaccaac   1380
ataaaatttt acttgtgcta ttataattta gctattaaat cctaaaatta tcaactgaaa   1440
gctactggaa aaataaatac ttctctttct ttttctccata ttgaaagtaa agagaatgag   1500
gatccttagc taagatttta attaaatctt ttctgagcca gaattgcaaa gcttttcttt   1560
gtataaataa ggactcgagt tataaagcat agaactagca atgagtctat cttggtccat   1620
ttggattgct ataaaggagt acctgaggct gggtaattta taaagaaaag acgtttattc   1680
gacacatgat tctgcaggat gtacaagaag catggcacca gcatctgctc ttggtgaaaa   1740
cttcaggtgg ctttgactcc tggtggaaga agggaagtct agcttgtgca gagctcccat   1800
ggccagagaa ggaagggggg tttgaggagg tgccaggctc tttgaataga gcgagaactc   1860
actcattacc aagagaaggc accaagccat tcatgaggga tacaccccctg tgacccaaac   1920
cttgcccccc ttccaacatt ggggcttaaa tttcaatgtg atgtttaggg gtacaaacat   1980
ccaaaccaca gcagagaaat acagagttct gtatttctat tcccaaaggg caaaatttgg   2040
gaggtgaatg ggtctatatg tgtgttgggg ggaagaagtt aatatgaaga aaagaaacta   2100
aagtgcttta cataataatg agaattacag attaaaaaat ctgtaatctt tccctaaaaa   2160
gggaaagaag taccatgcaa attatgaggt aagtagacta tatgacttat ttatttttat   2220
taggttagag caagaattgc aaactcaagg tcctgactcc ttgaattgca ctctatggac   2280
ccagtcatac ttcatttgca tattatatat taaatgcttt ggcatgatct ttgctccccc   2340
ttacatcctc aaaacactct ttttccattt ttcttaaaat atatgttcct ctttgtctat   2400
attttatttt tccaactttg aaaaggactt acacataaaa atggtatcac tttcttctta   2460
actgtaagaa aaatggtctc agccatacat tgatgaatgg cagctgtcat tcagcctcag   2520
tgtgaaggag acaacaatga gtggtgagga ctgtaataaa atggaaagca catgcccatc   2580
caaaagtgag cattcacttc taggaactag taaaaatggt aatagccaga tctttctatt   2640
ttttcacaag aagcctgaaa gtatttaaat attttatgac taattcaaat gctttaaaaa   2700
taagcaattt gattctagga ggccaaacta gttgctatct atgatttaaa ccatagtgtc   2760
tttcagaatt aatgtatgtc cttggcgggt gtgtgtgtgt gtgtgtgtgt gtgatcccaa   2820
aacaccaata attaccagtg aaaaatttag gagattaaat atgtgtactt taatccacat   2880
tgggggaaga gagagatata aaaggtgctg agaaccttga agtggtgccc ctcctgatct   2940
gccttctacc tcttcaacat acgtgctgtg caccatgaaa gacttgaagt gcaatggcaa   3000
tctgtgatcc tttgtggaaa cctttcccta atttgcccca gagtgaatgt ttcacacttg   3060
gattcacatt tgctgagaga ggcggaaaaa tcttagggac aattagaaca ataataacaa   3120
```

-continued

```
cattcatatt attattcaat gacagcaaca ttcatattca ttctttcatt cagcaaatat   3180
ttattgcaca cttgctatgt gctagaacta taaaatggca atgatgtgtt aggtaatttg   3240
taatcatggg gaaaaaatca gttagggaaa gacaaaactg ccttccctta tagagattat   3300
attcattgag gagacaaata ataaataaaa tgaatagtgt aacataggtt agatagtgac   3360
aagtgctatg gagaaaaaga aagtaggaaa gggtcatttc tctggtttcc tgatgtgtaa   3420
ttggaataga tatccttggt agctggtaga atctctgcag tgattccttg tactgtgggg   3480
taaaagctat gttagcaggg gagaccaaga ggaatagctg aaacaaaatt cactttctca   3540
gtaagatagt aaataagaaa gtgatattgc atcctgggaa acatggccga gattagtgct   3600
tctctttaag acctaaagga tgcagagtga tggccctcac tcatcctcat ttaattcacc   3660
tgtcaggccc ttgcaaaaat tggtctgatc ctgggggata ataaactcaa ccaaatagtt   3720
gccccaattg cttttgttat gcgagatata tctttgctag aacaaactga ttaacctggc   3780
ctcaggtacc ttgcattgat tggcaaatgt attcatttct attcctgtaa agaaagagaa   3840
acaaaagcac gggaatgaca cagactttta cagcactgag cagggctaat tctcatgccc   3900
tctgtcataa tataacctaa agggacttgg actgtctgga tactccgcac atcaacacca   3960
taacccacta tactgatgat atcatgtgtg atggttttca aatatgcaca caaatttctg   4020
attcttcttt cttcaagagg tggagcttaa ttccccttca attgagggtg agtcgggcat   4080
agtgacttgc ttctaattaa taaaatattg cagaagtgat gatgtggttt ttctaagaca   4140
ctgcaacttc ctttccttgc tctctcttga ataacatgct ctgaaggaaa tcaggtacta   4200
tgtgatgagg acattcaagc aatcctaggg agagattcat gtagaaaaga actaaggcct   4260
cctgccaaaa gccatttgag tcagccctct tggaagtaaa ccctctaccc ctagtaaagc   4320
cttcggatga ctgcagccct gggcagcatc ttgactgcaa actcatgaga gaccctgagc   4380
cacaatcacc cagctaagcc actcttaaat tcctgtccta tactgtgaga taataaatgt   4440
ttactggttt cagctgaaag gtgacagagt gggagtcatg tcaccatctc tggctgtaca   4500
cggaagaatt acagtgagtg acctttaaca caacccctta gtgctccttc ggtacccagt   4560
aaatgagggt tatcatacaa ctatgattat agagcaatag atctggctta ttcatgagac   4620
acttctgagc agtcataaat taaagcatgc atgcaaaagc ccaagatatg ccgttaacaa   4680
cactggaacc agacctcggt tttctcactt tattatctgt tctcctcttc tttggtttct   4740
ttttattttg ttttttttcca tcattgaatg atggtgaagt taataatgga aaagagggag   4800
ggaagaagag aagaaaggaa gttgaatata tgaaggacca aagagaatat taccttcctc   4860
cttctcgggt gtgcttagac acaaaaccta acatccaaat aaaccaaggt gtcatttgga   4920
tctctaatgg agattgccaa gagttctgta tgagacagat tcctattaaa gtctcagaac   4980
acgttctgtg caagatcatc tctggagagc atatatgttg ggaaaccctt ttccctctgc   5040
cttccctaaa tttggtctgg aacactgttt tggggtccac acatatcctt caacccaaca   5100
caatctcaac acaagaagag atcagggtaa atggggatca ggaaggaata tgtatccttc   5160
ttccagtcat gaatgaactt agatatcagg gggacaaatt tctgagtgtt atttctccat   5220
ggcttcccct gatgtggcct aagtgggtga ggaggcattt ttcccagccc ttatcaccca   5280
agtctttcta ttctggcccc tcagatagag acttggtaat acatcacttt tgttttggct   5340
gccctgcctg acccacctct cctctttcta acagaaaata gctgctgccc cactcctgtg   5400
ccaaaatctg ctccaaggga tcctatccta gtcagaaggc tgtactctga atgctgatat   5460
```

```
tagctacaac accaaggctt cccactatac aaactggatc ctcaaagtca tccacaccaa   5520

atgaactctc tattctttct cccagtagcc tgagaactgg gtttaccagc cttggccctt   5580

cctttccttc tagcctcaaa acaggatggg aacagagtct ttggctgtga gaatgggctc   5640

aataacaaaa taaagatgac agaagagtca gtgacttcaa tgacagagcg atagaaatta   5700

ccaatataaa cggagagaaa agagattttt taaaaatgaa caaatcccca aggacctgtg   5760

agacaataac tgtgttaggt tttctaaact tacaagtgtt tttatttata tatggtaagc   5820

aactatgcat tatttgtgtc agaattattt tttgtatata tttaaggtat acaacatgat   5880

gtctcaacat acttatatgt agtgaaatgg ttactacagt caccacactt attgtctcac   5940

aggttattgt cttcagaagg agagtaaaaa gaatgctggg tagaagaaat acctgaagaa   6000

ataatggccc aacctcaaat ttggtgaaag acataaactt acagattcaa gaaactgagt   6060

gttccccaaa cagaataaac tttaaagaat ccacactcaa acacatcata atcaaacttc   6120

tgaaaactaa caacaaagaa aaacttaaaa tcagcaagag agaaaccaca cattatcaac   6180

tgatgaaaag tgactcaagt gacagcagat ttataatcag aaacttgaag gacagaagga   6240

agaggcaaaa cattttgaaa gccctaaaag gaaagaactg tcaacccaga attcgacatc   6300

cagtaaaaat atccgtcaag aatgaatatg aaggaaagct aagaatgaat atatcttcta   6360

tttctttgct aaatttttct actttttcat ttgatgtaag agtgtttata agtgcttatg   6420

gagcattttt atgatagttg gtttacaatc cttgtctgag agtagctatg tgagatgacg   6480

tatatagtaa atggtgactg tagtaaccat ttcactacat ataagtatgt caaaacatgt   6540

tgtacacctt aaatatacac aaaaaatagc tctgacacaa aaaatgcata gttgttatta   6600

ccatgtataa ataaaaatac ttgtaagttt agaaaataaa atcattgtct gataattatc   6660

taaataataa agtcc                                                    6675


<210> SEQ ID NO 4
<211> LENGTH: 25
<212> TYPE: RNA
<213> ORGANISM: Artificial Sequence
<220> FEATURE:
<223> OTHER INFORMATION: siHERES_1 Sense Sequence

<400> SEQUENCE: 4

cacugugagu caggaucagu cuuau                                          25


<210> SEQ ID NO 5
<211> LENGTH: 25
<212> TYPE: RNA
<213> ORGANISM: Artificial Sequence
<220> FEATURE:
<223> OTHER INFORMATION: siHERES_1 Antisense Sequence

<400> SEQUENCE: 5

auaagacuga uccugacuca cagug                                          25


<210> SEQ ID NO 6
<211> LENGTH: 25
<212> TYPE: RNA
<213> ORGANISM: Artificial Sequence
<220> FEATURE:
<223> OTHER INFORMATION: siHERES_2 Sense Sequence

<400> SEQUENCE: 6

cacaccaaau gaacucucua uucuu                                          25
```

-continued

```
<210> SEQ ID NO 7
<211> LENGTH: 25
<212> TYPE: RNA
<213> ORGANISM: Artificial Sequence
<220> FEATURE:
<223> OTHER INFORMATION: siHERES_2 Antisense Sequence

<400> SEQUENCE: 7

aagaauagag aguucauuug gugug                                            25


<210> SEQ ID NO 8
<211> LENGTH: 32
<212> TYPE: DNA
<213> ORGANISM: Artificial Sequence
<220> FEATURE:
<223> OTHER INFORMATION: HERES WT

<400> SEQUENCE: 8

atatggaaaa ggtggtggag gtagaaagac at                                    32


<210> SEQ ID NO 9
<211> LENGTH: 19
<212> TYPE: DNA
<213> ORGANISM: Artificial Sequence
<220> FEATURE:
<223> OTHER INFORMATION: HERES-Mut

<400> SEQUENCE: 9

atatggaaaa gaaagacat                                                   19
```

PHARMACEUTICAL COMPOSITION CONTAINING HERES EXPRESSION INHIBITOR FOR PREVENTING OR TREATING SQUAMOUS CELL CARCINOMA

CROSS REFERENCE TO RELATED APPLICATIONS

This application is a National Stage of International Application No. PCT/KR2020/006064 filed May 8, 2020, claiming priority based on Korean Patent Application No. 10-2019-0067519 filed Jun. 7, 2019.

SEQUENCE LISTING

The content of the electronically submitted sequence listing, file name: Q270226_ST25.txt; size: 22,167 bytes; and date of creation: Jul. 9, 2025, filed herewith, is incorporated herein by reference in its entirety.

TECHNICAL FIELD

The present invention pertains to a pharmaceutical composition for preventing or treating squamous cell carcinoma, the pharmaceutical composition containing a highly expressed lncRNAs in esophageal squamous cell carcinoma (HERES) expression inhibitor. More specifically, the present invention pertains to a pharmaceutical composition which uses a HERES expression inhibitor to reduce the expression of HERES and affect Wnt signaling pathways, and thereby prevent or treat squamous cell carcinoma.

BACKGROUND ART

Squamous cell carcinoma is a carcinoma occurring in squamous cells such as the esophagus, head and neck, and lungs, and has been reported to have a poor prognosis due to a very high metastasis rate, and in particular, esophageal squamous cell carcinoma is known to have a 5 year survival rate of only 5 to 10%.

Meanwhile, in order to reliably treat cancer, patients with squamous cell carcinoma receive treatment such as radiation therapy and anticancer chemotherapy in advance, and then receive treatment to remove all tissues which are highly likely to develop cancer in advance.

In addition, since even a skilled doctor cannot be sure whether the above-mentioned cancer is treated before the surgical result of a patient with the squamous cell carcinoma condition is obtained, an affected part of the patient is excised as much as possible, such that patients who have undergone surgery are reported to have a poor quality of life and suffer from sequelae such as complications.

Thus, research on therapeutic agents capable of treating squamous cell carcinoma (J Cancer. 2016; 7(10): 1258-1264, Shen et al.) has been actively conducted, but is still insufficient, and there is a very urgent need for the development of a therapeutic agent capable of preventing or treating squamous cell carcinoma without a surgical operation.

DISCLOSURE

Technical Problem

The present inventors discovered that the expression pattern of highly expressed lncRNAs in esophageal squamous cell carcinoma (HERES) is related to the onset of squamous cell carcinoma, and confirmed that the HERES is a target for treating squamous cell carcinoma, and squamous cell carcinoma can be alleviated when the expression of HERES is inhibited, thereby completing the present invention.

Thus, an object of the present invention is to provide a pharmaceutical composition for preventing or treating squamous cell carcinoma, containing an HERES expression inhibitor as an active ingredient.

However, technical problems to be solved by the present invention are not limited to the aforementioned problems, and other problems that are not mentioned may be clearly understood by the person skilled in the art from the following description.

Technical Solution

To achieve the aforementioned object of the present invention, the present invention provides a pharmaceutical composition for preventing or treating squamous cell carcinoma, containing an HERES expression inhibitor as an active ingredient.

As an exemplary embodiment of the present invention, the HERES may include a base sequence represented by SEQ ID NO: 1 or 2.

As another exemplary embodiment of the present invention, the expression inhibitor may be any one selected from the group consisting of small interfering RNA (siRNA), short hairpin RNA (shRNA), micro RNA (miRNA), ribozymes, DNAzymes, peptide nucleic acids (PNAs), antisense oligonucleotides (ASOs) and chemical compounds.

As still another exemplary embodiment of the present invention, the composition may inhibit the expression of EZH2.

Further, the present invention provides a method for preventing or treating squamous cell carcinoma, the method including administering the pharmaceutical composition to an individual.

In addition, the present invention provides a use of the pharmaceutical composition for preventing or treating squamous cell carcinoma.

Advantageous Effects

The present inventors discovered that the expression pattern of highly expressed lncRNAs in esophageal squamous cell carcinoma (HERES) is related to the onset of squamous cell carcinoma, and found that HERES can be a target for treating squamous cell carcinoma. Accordingly, the pharmaceutical composition according to the present invention was determined to have the effect of inhibiting the proliferation, metastasis, and the like of squamous cell carcinoma due to containing the HERES expression inhibitor, and is thus expected to be advantageously used for preventing and treating or ameliorating squamous cell carcinoma.

DESCRIPTION OF DRAWINGS

FIG. 1 shows a schematic view illustrating an experimental process according to the present invention for verifying that highly expressed lncRNAs in esophageal squamous cell carcinoma (hereinafter, HERES) is a target for esophageal squamous cell carcinoma.

FIGS. 2A, 2B and 2C show the expression pattern of HERES, FIG. 2A shows the results of confirming the expression pattern of HERES in various esophageal squamous cell carcinoma cell lines, FIG. 2B shows the results of confirming the expression pattern of HERES in tissue samples derived from patients with esophageal squamous cell carcinoma, and FIG. 2C shows the results of confirming the correlation between the expression rate of HERES and the survival rate of patients with esophageal squamous cell carcinoma.

FIGS. 3A, 3B, 3C, 3D and 3E show changes in proliferation, metastasis, invasion and colony formation of esophageal squamous cell carcinoma due to inhibition of HERES expression, FIG. 3A shows the results of confirming the degree of proliferation of esophageal squamous cell carcinoma when the expression of HERESS is inhibited, FIG. 3B shows the results of confirming the difference in the degree of proliferation of esophageal squamous cell carcinoma before treatment with a HERES expression inhibitor and 48 hours after treatment with the inhibitor, FIG. 3C shows the results of confirming the proliferation of esophageal squamous cell carcinoma through cell staining when the expression of HERES is inhibited, FIG. 3D shows the results of confirming the degree of colony formation of esophageal squamous cell carcinoma when the expression of HERES is inhibited, and FIG. 3E shows the results of confirming the degree of metastasis or invasion of esophageal squamous cell carcinoma when the expression of HERES is inhibited by observing the presence or absence of protein expression of the factors involved in metastasis or invasion.

FIG. 4 shows the results of confirming the effect of inhibition of HERES expression on the expression of major genes related to the Wnt signaling pathway.

FIGS. 5A, 5B, 5C, 5D and 5E show the results confirming that HERES is involved in the epigenetic regulation of target genes through interaction with EZH2, FIG. 5A shows the results of confirming the direct interaction between HERES and an EZH2 protein, FIG. 5B shows the results of confirming the direct interaction between the EZH2 protein and a target gene, FIG. 5C shows the base sequences of the wild type of HERES (SEQ ID NO: 8, atatggaaaa ggtggtggag gtagaaagac at) and the mutant of HERES (SEQ ID NO: 9, atatggaaaa gaaagacat), FIG. 5D shows the results of confirming the expression levels of EZH2 protein and relative mRNA in the wild type of HERES and the mutant of HERES, and FIG. 5E shows the results of confirming the expression of HERES and the protein expression of CACNA2D3 in the wild type of HERES and the mutant of HERES.

FIGS. 6A, 6B and 6C show the results of verifying the therapeutic target potential of HERES for esophageal squamous cell carcinoma by xenograft experiments, FIG. 6A graphically shows the results of comparing the volumes of esophageal squamous epithelial cell cancer cells in the control with the case where the expression of HERES is inhibited, FIG. 6B shows the results of comparing the volumes of esophageal squamous cell carcinoma cells in the control by the naked eye with the case where the expression of HERES is inhibited, and FIG. 6C graphically shows the results of comparing the weights of esophageal squamous cell carcinoma cells in the control with the case where the expression of HERES is inhibited.

MODES OF THE INVENTION

Hereinafter, the present invention will be described in detail.

The present inventors discovered that the expression pattern of highly expressed lncRNAs in esophageal squamous cell carcinoma (hereinafter, HERES), which is a long non-coding RNA, is related to the onset of squamous cell carcinoma, and found that HERES can be a target for treating squamous cell carcinoma, and thus confirmed that the present invention could inhibit proliferation, metastasis, and the like by inhibiting the expression of HERES, thereby completing the present invention.

Thus, the present invention provides a pharmaceutical composition for preventing or treating squamous cell carcinoma, containing an HERES expression inhibitor as an active ingredient.

"Squamous cell carcinoma", which is the target disease of the present invention, is a malignant tumor derived from keratinocytes of the epidermis. Squamous cell carcinoma is a non-melanoma skin cancer which is more complex than basal cell carcinoma in terms of biological aspects such as metastasis according to tumor size and depth, cause, anatomical location, and histological characteristics, and is one of the most commonly occurring skin cancers along with basal cell carcinoma in Korea. Further, squamous cell carcinoma occurs not only on the skin but also on the mucous membranes, its symptoms vary depending on the site of occurrence and the cause, and the cancer generally looks like a broken chunk of flesh with a relatively large and uneven shape, and since the surface of the tumor (carcinoma) becomes weak at the onset of squamous cell carcinoma, infection by general bacteria is likely to occur, and although there may be pus or a foul odor, it is reported that there are no other subjective symptoms. Types thereof include squamous cell carcinoma arising from sun-damaged skin, and squamous cell carcinoma arising from cicatrices (scars) and chronic inflammatory diseases, arsenic-induced squamous cell carcinoma, radioactivity-induced squamous cell carcinoma, de novo squamous cell carcinoma or verrucous carcinoma depending on the cause, and include squamous cell carcinoma of the face, neck, arms, and the like, squamous cell carcinoma originating in the lungs, squamous cell carcinoma originating in the esophagus and squamous cell carcinoma originating in the head and neck depending on the site of occurrence, but are not limited thereto.

The HERES according to the present invention may include a base sequence represented by SEQ ID NO: 1 or 2. In this case, it is also possible to include a base sequence having a sequence homology of 70% or more, preferably 80% or more, more preferably 90% or more, and most preferably 95%, 96%, 97%, 98%, or 99% or more with the base sequence represented by SEQ ID NO: 1 or 2.

Further, an HERES gene encoding the HERES according to the present invention may include a base sequence represented by SEQ ID NO: 3.

As used herein, the term "expression inhibition" means that the function of a target gene is degraded, and means that preferably the expression of the target gene becomes undetectable or is present at an insignificant level The expression inhibitor according to the present invention may be any one selected from the group consisting of small interfering RNA (siRNA), short hairpin RNA (shRNA), micro RNA (miRNA), ribozymes, DNAzymes, peptide nucleic acids (PNAs), antisense oligonucleotides (ASOs) and chemical compounds, and preferably siRNA or antisense oligonucleotides (ASOs), but is not limited thereto.

The small interfering RNA (siRNA) according to the present invention means a short double-stranded RNA capable of inducing an RNA interference (RNAi) phenomenon through cleavage of a specific mRNA. The siRNA according to the present invention includes a sense RNA strand having a sequence homologous with the mRNA of the target gene and an antisense RNA having a sequence complementary thereto. Since the siRNA can inhibit the expression of the target gene, it is provided as an efficient gene knockdown method or by a gene therapy method.

The antisense oligonucleotide (ASO) according to the present invention means an oligonucleotide capable of regulating the expression of the target gene by hybridizing with a target nucleic acid, particularly an adjacent sequence on the target nucleic acid.

The composition according to the present invention may prevent or treat squamous cell carcinoma by inhibiting the function of EZH2 to regulate the Wnt signaling pathway, thereby reducing the proliferation, metastasis, invasion and colony formation of squamous cell carcinoma.

The enhancer of zeste homolog 2 (EZH2) according to the present invention is a histone-lysine N-methyltransferase encoded by the EZH2 gene. The EZH2 mediates the reaction of adding a methyl group to histone H3 of lysine 27 using a cofactor S-adenosyl-L-methionine. The methylation activity of EZH2 serves to silence gene function by promoting the formation of a heterochromatin. In addition, EZH2 is a functional enzyme component of polycomb repressive complex 2 (PRC2), and it is reported that EZH2 serves to maintain embryonic development by epigenetic regulation of genes involved in the regulation of development and differentiation.

The present inventors identified the HERES as a target candidate for the treatment of esophageal squamous cell carcinoma by confirming changes in the expression pattern of HERES in various esophageal squamous cell carcinoma cell lines and tissues derived from patients with esophageal epithelial cell carcinoma.

Thus, in an embodiment of the present invention, it was verified that when the expression of HERES is inhibited using siHERES, the proliferation, metastasis, invasion and colony formation of esophageal squamous cell carcinoma were reduced (see Example 3).

Furthermore, in another embodiment of the present invention, it was verified that when the expression of HERES is inhibited using siHERES, tumor volume and tumor weight are reduced (see Example 5).

Through the above example results, it was confirmed that when the expression of HERES was inhibited in esophageal squamous cell carcinoma cells, the proliferation, metastasis, and the like of esophageal squamous cell carcinoma were effectively reduced, so that it could be confirmed that HERES is a very promising target for treatment.

The pharmaceutical composition according to the present invention may contain the HERES expression inhibitor as an active ingredient and further include a pharmaceutically acceptable carrier. The pharmaceutically acceptable carrier is typically used in formulation, and includes saline, sterile water, Ringer's solution, buffered saline, cyclodextrin, a dextrose solution, a maltodextrin solution, glycerol, ethanol, liposomes, and the like, but is not limited thereto, and may further include other typical additives such as an antioxidant and a buffer, if necessary. Further, the oral composition according to the present invention may be formulated into an injectable formulation, such as an aqueous solution, a suspension, and an emulsion, a pill, a capsule, a granule, or a tablet by additionally adding a diluent, a dispersant, a surfactant, a binder, a lubricant, and the like. With regard to suitable pharmaceutically acceptable carriers and formulations, the composition may be preferably formulated according to each ingredient by using the methods disclosed in Remington's literature. The pharmaceutical composition of the present invention is not particularly limited in formulation, but may be formulated into an injection, an inhalant, an external preparation for skin, or the like.

The pharmaceutical composition of the present invention may be orally administered or may be parenterally administered (for example, applied intravenously, subcutaneously, intraperitoneally, or locally), but may be preferably orally administered, and the administration dose may vary depending on a patient's condition and body weight, severity of disease, drug form, and administration route and period according to the target method, but the administration dose may be properly selected by those skilled in the art.

The pharmaceutical composition of the present invention is administered in a pharmaceutically effective amount. As used herein, the "pharmaceutically effective amount" refers to an amount sufficient for treating or diagnosing diseases at a reasonable benefit/risk ratio applicable to medical treatment or diagnosis, and an effective dosage level may be determined according to factors including the type of disease of patients, the severity of disease, the activity of drugs, sensitivity to drugs, administration time, administration route, excretion rate, treatment period, and simultaneously used drugs, and other factors well known in the medical field. The pharmaceutical composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount may be easily determined by those skilled in the art.

Specifically, an effective amount of the pharmaceutical composition of the present invention may vary depending on the age, sex, condition, and body weight of a patient, the absorption of the active ingredient in the body, inactivation rate and excretion rate, disease type, and the drugs used in combination, and in general, 0.001 to 150 mg, preferably 0.001 to 100 mg of the pharmaceutical composition of the present invention per 1 kg of a body weight may be administered daily or every other day or may be dividedly administered once to three times a day. However, since the effective amount may be increased or decreased depending on the administration route, the severity of obesity, gender, body weight, age, and the like, the dosage is not intended to limit the scope of the present invention in any way.

As another aspect of the present invention, the present invention provides a method for preventing or treating squamous cell carcinoma, the method including administering the pharmaceutical composition to an individual.

The "an individual" as used herein refers to a subject in need of treatment of a disease, and more specifically, refers to a mammal such as a human or a non-human primate, a mouse, a rat, a dog, a cat, a horse, and a cow.

As still another aspect of the present invention, the present invention provides a use of the pharmaceutical composition for preventing or treating squamous cell carcinoma.

Hereinafter, preferred examples for helping the understanding of the present invention will be suggested. However, the following examples are provided only to more easily understand the present invention, and the contents of the present invention are not limited by the following examples.

EXAMPLES

Example 1. Experimental Preparation and Experimental Methods 1-1. Production of esophageal squamous cell carcinoma RNA-seq data After esophageal tissue excised from a patient with esophageal squamous cell carcinoma was subjected to homogenization, RNA was extracted to perform RNA analysis. For RNA extraction, cell constituents excluding RNA, DNA and proteins were removed using the Trizol reagent, and then RNA, DNA and proteins were isolated using chloroform. After an RNA layer was extracted from the separated layer, RNA was washed and deposited. After pellets were made by precipitating RNA, an RNA sample was obtained by dissolving the pellets in nuclease-free water. Sequencing was performed from the RNA sample using Illumina Hiseq 2000.

1-2. Inhibition of HERES Expression Using siRNA

After two HERES siRNAs (siHERES_1, siHERES_2) were constructed, esophageal cancer cells prepared on a 6-well plate were transfected using the Lipofectamine 2000 reagent. In this case, in order to prevent inhibition of liposome formation, it was replaced with serum-free media.

After scrambled RNA was equally transfected in order to be used as a control for inhibition of HERES expression by siRNA, the inhibition of HERES expression was confirmed compared to the control after 48 hours.

Example 2. Confirmation of Expression Pattern of Long Non-Coding RNA HERES in Esophageal Squamous Cell Carcinoma Cell Lines and Patient-Derived Samples

2-1. Selection of Target for Treating Esophageal Squamous Cell Carcinoma

A target for treating esophageal squamous cell carcinoma was selected by the following process, as shown in FIG. 1.

1924 long non-coding RNAs with changing expression patterns at the onset of esophageal squamous cell carcinoma were selected by analyzing Korean esophageal squamous cell carcinoma RNA-seq data. Next, by analyzing the correlation between the differential expression of long non-coding RNA in YSH (n=66) and TCGA (n=95) and the survival rate of patients with esophageal squamous cell carcinoma, HERES, which showed significant results, was selected as a target for treating esophageal squamous cell carcinoma, as illustrated in FIG. 2C. More specifically, it was confirmed that overexpression of HERES reduces the survival rate of patients with esophageal squamous cell carcinoma.

2-2. Confirmation of Expression Pattern of HERES in Esophageal Squamous Cell Carcinoma Cell Lines and Patient-Derived Samples Based on the results of Example 2-1, an experiment was performed to verify whether HERES, which shows a change in expression pattern in esophageal squamous cell carcinoma, is expressed in various esophageal squamous cell carcinoma cell lines and patient-derived samples.

As a result, as illustrated in FIGS. 2A and 2B, it was confirmed that HERES was overexpressed not only in various esophageal squamous cell carcinoma cell lines but also in patient-derived tissue samples.

Example 3. Verification of Changes in Proliferation, Metastasis, Invasion, and colony formation of esophageal squamous cell carcinoma cell lines according to inhibition of HERES expression Based on the results of Example 2, in order to verify whether HERES, which is specifically overexpressed in patients with esophageal squamous cell carcinoma, may be a target for treating esophageal squamous cell carcinoma, an in vitro experiment was performed to confirm changes in proliferation, metastasis, invasion, and colony formation of esophageal squamous cell carcinoma cell lines due to inhibition of HERES expression by the use of siHERES.

As a result, as illustrated in FIGS. 3A to 3E, it was confirmed that when HERES expression is inhibited, the growth, metastasis, invasion and colony formation of esophageal squamous cell carcinoma is inhibited.

More specifically, as illustrated in FIGS. 3A to 3C, it was confirmed that when the expression of HERES in KYSE-30 and HCE-7 is inhibited, the degree of proliferation of esophageal squamous cell carcinoma is reduced compared to the control.

Furthermore, as illustrated in FIG. 3D, it was confirmed that when the expression of HERES in KYSE-30 and HCE-7 is inhibited, the degree of colony formation of esophageal squamous cell carcinoma is lower than that of the control.

Further, as illustrated in FIG. 3E, it was confirmed that when the expression of HERES in KYSE-30 and HCE-7 is inhibited, the expression of N-cadherin and vimentin, which are related to the metastasis or invasion of esophageal squamous cell carcinoma is lower than that of the control.

Example 4. Verification of Changes in Major Factors of Wnt Signaling Pathway According to Inhibition of HERES Expression An experiment was performed to confirm that HERES regulates major genes related to the Wnt signaling pathway.

As a result, as illustrated in FIG. 4, it was confirmed that the inhibition of expression of HERES in KYSE-30 and HCE-7 affects the expression of major factors involved in the Wnt signaling pathway. More specifically, it was confirmed that the expression of CACNA2D3 among the major factors involved in the Wnt signaling pathway was increased.

In addition, additional RIP, mutagenesis assay, and FISH experiments were performed to confirm that HERES regulates major genes related to the Wnt signaling pathway.

As a result, as illustrated in FIGS. 5A to 5E, it was confirmed through the RIP, mutagenesis assay, and FISH experiments that HERES and EZH2 interacted with each other to epigenetically regulate target genes.

More specifically, as illustrated in FIGS. 5A and 5B, it was confirmed that HERES and EZH2 directly interacted with each other in KYSE-30, and that EZH2 and the target gene directly interacted with each other.

In addition, as illustrated in FIGS. 5C and 5D, it was confirmed through the base sequences of the wild type of HERES and the mutant (removal of sequence interacting with EZH2) of HERES that the relative expression levels of the EZH2 protein and mRNA were changed.

Furthermore, as illustrated in FIG. 5E, it was confirmed through the base sequences of the wild type of HERES and the mutant of HERES that the interaction of HERES and EZH2 regulated the expression of the CACNA2D3 protein.

Example 5. Verification of Effect of Inhibition of HERES Expression on Tumor Volume and Weight A xenograft experiment was performed to confirm that HERES regulates major genes related to the Wnt signaling pathway.

As a result, as illustrated in FIGS. 6A to 6C, it was confirmed that the inhibition of HERES expression directly affects tumor volume and tumor weight.

More specifically, it was confirmed in FIG. 6B that when the expression of HERES is inhibited using siHERES including the base sequences described in the following Tables 1 and 2, tumor volume is reduced, and in FIG. 6C that when the expression of HERES is inhibited using siHERES, tumor weight is reduced.

TABLE 1

| Classification | siHERES_1 |
|---|---|
| Sense (SEQ ID NO: 4) | CAC UGU GAG UCA GGA UCA GUC UUA U |
| Antisense (SEQ ID NO: 5) | A UAA GAC UGA UCC UGA CUC ACA GUG |

TABLE 2

| Classification | siHERES_2 |
|---|---|
| Sense (SEQ ID NO: 6) | CAC ACC AAA UGA ACU CUC UAU UCU U |
| Antisense (SEQ ID NO: 7) | A AGA AU A GAG AGU UC A UUU GGU GUG |

From the above results, it was possible to confirm the potential of HERES as a target for treating esophageal squamous cell carcinoma.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described embodiments are only exemplary in all aspects and are not restrictive.

INDUSTRIAL APPLICABILITY

Since the present invention is a technique capable of developing a therapeutic agent for squamous cell carcinoma by regulating a Wnt signaling gene related to the proliferation and metastasis of squamous cell carcinoma using siRNA which inhibits the expression of HERES, which is a non-coding RNA affecting the onset of squamous cell carcinoma, it is possible to develop a therapeutic agent with a wider range of application and higher stability than therapeutic agents in the related art, and since the HERES gene can be usefully used to predict the proliferation and metastasis of a disease as a marker for predicting the prognosis of squamous cell carcinoma, the technique according to the present invention is expected to be widely utilized in the fields of prognosis prediction and the development of a therapeutic agent for squamous cell carcinoma. Further, the technique can be generally used in the fields of prognosis of carcinomas and development of a therapeutic agent for carcinomas, caused by problems with the Wnt signaling system.

The invention claimed is:

1. A method for treating esophageal squamous cell carcinoma in an individual in need thereof, the method comprising administering, to the individual, an effective amount of a pharmaceutical composition comprising a Highly Expressed lncRNAs in Esophageal Squamous Cell Carcinoma (HERES) expression inhibitor as an active ingredient, wherein the HERES expression inhibitor is a small interfering RNA (siRNA) comprising the sequences of SEQ ID NO: 4 and SEQ ID NO: 5, or SEQ ID NO: 6 and SEQ ID NO: 7; and HERES is the nucleotide sequence comprising the sequence of SEQ ID NO: 1 or SEQ ID NO: 2.

2. The method of claim 1, wherein the HERES consists of the nucleotide sequence of SEQ ID NO: 1 or SEQ ID NO: 2.

3. The method of claim 1, wherein the HERES expression inhibitor in the pharmaceutical composition inhibits protein expression of Enhancer of Zeste Homolog 2 (EZH2).

* * * * *